(12) United States Patent
Kienzle et al.

(10) Patent No.: US 9,610,007 B2
(45) Date of Patent: *Apr. 4, 2017

(54) FULLY INTEGRATED, DISPOSABLE TISSUE VISUALIZATION DEVICE

(71) Applicant: Trice Medical, Inc., King of Prussia, PA (US)

(72) Inventors: Richard A. Kienzle, Malvern, PA (US); Richard H. Washburn, II, Wayne, PA (US); Richard T. Briganti, Philadelphia, PA (US); Carl Deirmengian, Newton Square, PA (US)

(73) Assignee: Trice Medical, Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/187,583

(22) Filed: Jun. 20, 2016

(65) Prior Publication Data

US 2016/0296108 A1    Oct. 13, 2016

Related U.S. Application Data

(63) Continuation of application No. 14/308,167, filed on Jun. 18, 2014, now Pat. No. 9,370,295.

(Continued)

(51) Int. Cl.
*A61B 1/04* (2006.01)
*A61B 1/00* (2006.01)
(Continued)

(52) U.S. Cl.
CPC ............... *A61B 1/07* (2013.01); *A61B 1/002* (2013.01); *A61B 1/00009* (2013.01);
(Continued)

(58) Field of Classification Search
CPC .. A61B 1/07; A61B 1/34; A61B 1/045; A61B 1/00114; A61B 1/012; A61B 1/0008; A61B 1/00052; A61B 1/317

See application file for complete search history.

(56) References Cited

U.S. PATENT DOCUMENTS

| 4,069,823 | A | 1/1978 | Isakov et al. |
| 4,519,391 | A | 5/1985 | Murakoshi |

(Continued)

FOREIGN PATENT DOCUMENTS

| CN | 2557085 Y | 6/2003 |
| CN | 1612708 A | 5/2005 |

(Continued)

OTHER PUBLICATIONS

U.S. Appl. No. 15/187,583, filed Jun. 20, 2016, Kienzle et al.
(Continued)

*Primary Examiner* — Timothy J Neal
(74) *Attorney, Agent, or Firm* — Knobbe, Martens, Olson & Bear LLP

(57) ABSTRACT

The present invention relates to a fully integrated sterilizable one time use disposable tissue visualization device and methods for using such devices. Preferred embodiments of the invention facilitate the visualization of an internal tissue site while causing a minimum of damage to the surrounding tissue. Further preferred embodiments may allow for the delivery of fluids and other treatment to an internal tissue site.

29 Claims, 12 Drawing Sheets

Related U.S. Application Data

(60) Provisional application No. 61/926,578, filed on Jan. 13, 2014.

(51) Int. Cl.

| | | |
|---|---|---|
| *A61B 1/07* | (2006.01) | |
| *A61B 17/34* | (2006.01) | |
| *A61B 1/012* | (2006.01) | |
| *A61B 1/002* | (2006.01) | |
| *A61B 1/045* | (2006.01) | |
| *A61B 1/06* | (2006.01) | |
| *A61B 17/00* | (2006.01) | |

(52) U.S. Cl.
CPC ........ *A61B 1/0011* (2013.01); *A61B 1/00045* (2013.01); *A61B 1/00066* (2013.01); *A61B 1/00087* (2013.01); *A61B 1/00098* (2013.01); *A61B 1/00103* (2013.01); *A61B 1/00114* (2013.01); *A61B 1/00163* (2013.01); *A61B 1/012* (2013.01); *A61B 1/045* (2013.01); *A61B 1/0684* (2013.01); *A61B 17/34* (2013.01); *A61B 17/3468* (2013.01); *A61B 2017/0023* (2013.01)

(56) References Cited

U.S. PATENT DOCUMENTS

| | | |
|---|---|---|
| 4,624,243 A | 11/1986 | Lowery et al. |
| 4,646,738 A | 3/1987 | Trott |
| 4,651,201 A | 3/1987 | Schoolman |
| 4,678,459 A | 7/1987 | Onik et al. |
| 4,697,210 A | 9/1987 | Toyota et al. |
| 4,700,702 A | 10/1987 | Nilsson |
| 4,750,902 A | 6/1988 | Wuchinich et al. |
| 4,845,555 A | 7/1989 | Yabe et al. |
| 4,919,112 A | 4/1990 | Siegmund |
| 5,088,676 A | 2/1992 | Orchard et al. |
| 5,131,382 A | 7/1992 | Meyer |
| 5,170,775 A | 12/1992 | Tagami |
| 5,178,130 A | 1/1993 | Kaiya |
| 5,188,093 A | 2/1993 | Lafferty et al. |
| 5,190,028 A | 3/1993 | Lafferty et al. |
| 5,195,541 A | 3/1993 | Obenchain |
| 5,228,430 A | 7/1993 | Sakamoto |
| 5,242,441 A | 9/1993 | Avitall |
| 5,269,785 A | 12/1993 | Bonutti |
| 5,291,010 A | 3/1994 | Tsuji |
| 5,312,407 A | 5/1994 | Carter |
| 5,313,962 A | 5/1994 | Obenchain |
| 5,318,589 A | 6/1994 | Lichtman |
| 5,373,312 A | 6/1994 | Bala |
| 5,334,183 A | 8/1994 | Wuchinich |
| 5,351,678 A | 10/1994 | Clayton et al. |
| 5,354,302 A | 10/1994 | Ko |
| 5,365,267 A | 11/1994 | Edwards |
| 5,368,015 A | 11/1994 | Wilk |
| 5,369,525 A | 11/1994 | Bala et al. |
| 5,373,317 A | 12/1994 | Salvati et al. |
| 5,373,392 A | 12/1994 | Bala |
| 5,383,888 A | 1/1995 | Zvenyatsky et al. |
| 5,395,313 A | 3/1995 | Naves et al. |
| 5,403,276 A | 4/1995 | Schechter et al. |
| 5,403,342 A | 4/1995 | Tovey et al. |
| 5,417,203 A | 5/1995 | Tovey et al. |
| 5,423,312 A | 6/1995 | Siegmund et al. |
| 5,425,355 A | 6/1995 | Kulick |
| 5,476,473 A | 12/1995 | Heckele |
| 5,484,433 A | 1/1996 | Taylor et al. |
| 5,494,483 A | 2/1996 | Adair |
| 5,500,012 A | 3/1996 | Brucker et al. |
| 5,512,036 A | 4/1996 | Tamburrino et al. |
| 5,518,502 A | 5/1996 | Kaplan et al. |
| 5,547,455 A | 8/1996 | McKenna et al. |
| 5,569,158 A | 10/1996 | Suzuki et al. |
| 5,577,992 A | 11/1996 | Chiba et al. |
| 5,591,192 A | 1/1997 | Privitera et al. |
| 5,601,525 A | 2/1997 | Okada |
| 5,630,784 A | 5/1997 | Siegmund et al. |
| 5,630,837 A | 5/1997 | Crowley |
| 5,643,294 A | 7/1997 | Tovey et al. |
| 5,647,840 A | 7/1997 | D'Amelio et al. |
| 5,674,191 A | 10/1997 | Edwards et al. |
| 5,695,513 A | 12/1997 | Johnson et al. |
| 5,704,534 A | 1/1998 | Huitema et al. |
| 5,707,382 A | 1/1998 | Sierocuk et al. |
| 5,713,505 A | 2/1998 | Huitema |
| 5,722,403 A | 3/1998 | McGee et al. |
| 5,735,792 A | 4/1998 | Vanden Hoeck et al. |
| 5,766,194 A | 6/1998 | Smith |
| 5,766,199 A | 6/1998 | Heisler et al. |
| 5,766,200 A | 6/1998 | Mazurek et al. |
| 5,785,647 A | 7/1998 | Tompkins et al. |
| 5,788,636 A | 8/1998 | Curley |
| 5,818,527 A | 10/1998 | Yamaguchi et al. |
| 5,836,943 A | 11/1998 | Miller, III |
| 5,857,961 A | 1/1999 | Vanden Hoeck et al. |
| 5,864,359 A | 1/1999 | Kazakevich |
| 5,868,664 A | 2/1999 | Speier et al. |
| 5,873,814 A | 2/1999 | Adair |
| 5,873,816 A | 2/1999 | Kagawa et al. |
| 5,879,285 A | 3/1999 | Ishii |
| 5,888,193 A | 3/1999 | Breidental et al. |
| 5,902,272 A | 5/1999 | Eggers et al. |
| 5,916,146 A | 6/1999 | Allotta et al. |
| 5,928,137 A | 7/1999 | Green |
| 5,929,901 A | 7/1999 | Adair et al. |
| 5,941,817 A | 8/1999 | Crawford |
| 5,976,075 A | 11/1999 | Beane et al. |
| 5,976,076 A | 11/1999 | Kolff et al. |
| 5,976,077 A | 11/1999 | Wittens et al. |
| 5,986,693 A | 11/1999 | Adair et al. |
| 6,001,084 A | 12/1999 | Riek et al. |
| 6,043,839 A | 3/2000 | Adair et al. |
| 6,045,549 A | 4/2000 | Smethers et al. |
| 6,053,923 A | 4/2000 | Veca et al. |
| 6,068,603 A | 5/2000 | Suzuki |
| 6,080,101 A | 6/2000 | Tatsuno et al. |
| 6,086,528 A | 7/2000 | Adair |
| 6,099,465 A | 8/2000 | Inoue |
| 6,110,127 A | 8/2000 | Suzuki |
| 6,112,123 A | 8/2000 | Kelleher et al. |
| 6,113,614 A | 9/2000 | Mears |
| 6,126,592 A | 10/2000 | Proch et al. |
| 6,142,957 A | 11/2000 | Diamond et al. |
| 6,149,646 A | 11/2000 | West, Jr. et al. |
| 6,156,033 A | 12/2000 | Tu et al. |
| 6,211,904 B1 | 4/2001 | Adair et al. |
| 6,241,727 B1 | 6/2001 | Tu et al. |
| 6,251,120 B1 | 6/2001 | Dorn |
| 6,261,226 B1 | 7/2001 | McKenna et al. |
| 6,264,670 B1 | 7/2001 | Chin |
| 6,275,255 B1 | 8/2001 | Adair et al. |
| 6,277,137 B1 | 8/2001 | Chin |
| 6,310,642 B1 | 10/2001 | Adair et al. |
| 6,315,712 B1 | 11/2001 | Rovegno |
| 6,316,215 B1 | 11/2001 | Adair et al. |
| 6,322,494 B1 | 11/2001 | Bullicant et al. |
| 6,331,165 B1 | 12/2001 | Turturro et al. |
| 6,332,881 B1 | 12/2001 | Carner et al. |
| 6,387,043 B1 | 5/2002 | Yoon |
| 6,390,972 B1 | 5/2002 | Speier et al. |
| 6,419,626 B1 | 7/2002 | Yoon |
| 6,419,627 B1 | 7/2002 | Ben Nun |
| 6,419,654 B1 | 7/2002 | Kadan |
| 6,424,369 B1 | 7/2002 | Adair et al. |
| 6,452,626 B1 | 9/2002 | Adair et al. |
| 6,458,140 B2 | 10/2002 | Akin et al. |
| 6,464,633 B1 | 10/2002 | Hosoda et al. |
| 6,464,711 B1 | 10/2002 | Emans et al. |
| 6,468,274 B1 | 10/2002 | Alleyne et al. |
| 6,478,730 B1 | 11/2002 | Bala et al. |
| 6,491,690 B1 | 12/2002 | Goble et al. |
| 6,527,753 B2 | 3/2003 | Sekine et al. |

(56) References Cited

U.S. PATENT DOCUMENTS

| | | |
|---|---|---|
| 6,533,749 B1 | 3/2003 | Mitusina et al. |
| 6,544,194 B1 | 4/2003 | Kortenbach et al. |
| 6,561,973 B1 | 5/2003 | Bala |
| 6,569,085 B2 | 5/2003 | Kortenbach et al. |
| 6,572,578 B1 | 6/2003 | Blanchard |
| 6,583,240 B2 | 6/2003 | Merrick-Mack et al. |
| 6,585,734 B2 | 7/2003 | Levinson |
| 6,602,247 B2 | 8/2003 | Lalonde |
| 6,602,248 B1 | 8/2003 | Sharps et al. |
| 6,605,087 B2 | 8/2003 | Swartz et al. |
| 6,607,529 B1 | 8/2003 | Jones et al. |
| 6,623,437 B2 | 9/2003 | Hinchliffe et al. |
| 6,632,227 B2 | 10/2003 | Adams |
| 6,652,522 B2 | 11/2003 | Cucin |
| 6,656,132 B1 | 12/2003 | Ouchi |
| 6,656,195 B2 | 12/2003 | Peters et al. |
| 6,660,011 B2 | 12/2003 | Levinson |
| 6,675,033 B1 | 1/2004 | Lardo et al. |
| 6,679,838 B2 | 1/2004 | Bala |
| 6,682,535 B2 | 1/2004 | Hoogland |
| 6,689,130 B2 | 2/2004 | Arai et al. |
| 6,692,432 B1 | 2/2004 | Yarush et al. |
| 6,695,772 B1 | 2/2004 | Bon et al. |
| 6,726,684 B1 | 4/2004 | Woloszko et al. |
| 6,750,037 B2 | 6/2004 | Adair et al. |
| 6,764,439 B2 | 7/2004 | Schaaf et al. |
| 6,805,715 B2 | 10/2004 | Reuter et al. |
| 6,820,791 B2 | 11/2004 | Adams |
| 6,832,984 B2 | 12/2004 | Stelzer et al. |
| 6,833,000 B2 | 12/2004 | Levinson |
| 6,835,198 B2 | 12/2004 | Bonutti |
| 6,837,887 B2 | 1/2005 | Woloszko et al. |
| 6,862,036 B2 | 3/2005 | Adair et al. |
| 6,863,651 B2 | 3/2005 | Remijan et al. |
| 6,893,436 B2 | 5/2005 | Woodard et al. |
| 6,899,672 B2 | 5/2005 | Chin et al. |
| 6,902,526 B2 | 6/2005 | Katzman |
| 6,982,740 B2 | 1/2006 | Adair et al. |
| 6,982,742 B2 | 1/2006 | Adair et al. |
| 6,997,941 B2 | 2/2006 | Sharkey et al. |
| 7,002,621 B2 | 2/2006 | Adair et al. |
| 7,004,938 B2 | 2/2006 | Ormsby et al. |
| 7,030,904 B2 | 4/2006 | Adair et al. |
| 7,060,028 B2 | 6/2006 | Luloh et al. |
| 7,094,200 B2 | 8/2006 | Katzman |
| 7,108,657 B2 | 9/2006 | Irion et al. |
| 7,137,981 B2 | 11/2006 | Long |
| 7,156,559 B2 | 1/2007 | Gauthier, Jr. et al. |
| 7,160,247 B2 | 1/2007 | Deppmeier et al. |
| 7,160,295 B1 | 1/2007 | Garito et al. |
| 7,169,147 B2 | 1/2007 | Nosel |
| 7,179,255 B2 | 2/2007 | Lettice et al. |
| 7,198,635 B2 | 4/2007 | Danek et al. |
| 7,214,183 B2 | 5/2007 | Miyake |
| 7,258,663 B2 | 8/2007 | Doguchi et al. |
| 7,269,344 B2 | 9/2007 | Nishioka et al. |
| 7,270,658 B2 | 9/2007 | Woloszko et al. |
| 7,318,823 B2 | 1/2008 | Sharps et al. |
| 7,320,688 B2 | 1/2008 | Foley et al. |
| RE40,156 E | 3/2008 | Sharps et al. |
| 7,435,010 B2 | 10/2008 | Gauthier, Jr. et al. |
| 7,453,984 B2 | 11/2008 | Chen et al. |
| 7,491,168 B2 | 2/2009 | Raymond et al. |
| 7,572,578 B2 | 2/2009 | Blanchard |
| 7,689,268 B2 | 3/2010 | Marshik-Geurts et al. |
| 7,699,773 B2 | 4/2010 | Forkey et al. |
| 7,708,689 B2 | 5/2010 | Deppmeier et al. |
| 7,857,755 B2 | 12/2010 | Kupferschmid et al. |
| 7,918,787 B2 | 4/2011 | Saadat |
| 7,942,814 B2 | 5/2011 | Remijan et al. |
| 8,016,839 B2 | 9/2011 | Wilk |
| 8,038,602 B2 | 10/2011 | Gill et al. |
| 8,046,057 B2 | 10/2011 | Clarke |
| 8,052,609 B2 | 11/2011 | Harhen |
| 8,142,346 B2 | 3/2012 | Shoroji et al. |
| 8,170,319 B2 | 5/2012 | Shukla |
| 8,277,411 B2 | 10/2012 | Gellman |
| 8,317,689 B1 | 11/2012 | Remijan et al. |
| 8,475,361 B2 | 7/2013 | Barlow et al. |
| 8,885,034 B2 | 11/2014 | Adair et al. |
| 2001/0036015 A1 | 11/2001 | Eguchi |
| 2001/0053873 A1 | 12/2001 | Schaaf et al. |
| 2002/0007110 A1 | 1/2002 | Irion |
| 2002/0087047 A1 | 7/2002 | Remijan et al. |
| 2002/0177847 A1 | 11/2002 | Long |
| 2003/0040668 A1 | 2/2003 | Kaneko et al. |
| 2003/0120156 A1 | 6/2003 | Forrester et al. |
| 2003/0181905 A1 | 9/2003 | Long |
| 2003/0233024 A1 | 12/2003 | Ando |
| 2004/0102772 A1 | 5/2004 | Baxter et al. |
| 2004/0162554 A1 | 8/2004 | Lee et al. |
| 2004/0162572 A1 | 8/2004 | Sauer |
| 2004/0215061 A1 | 10/2004 | Kimmel et al. |
| 2005/0038317 A1 | 2/2005 | Ratnakar |
| 2005/0090762 A1 | 4/2005 | Burbank et al. |
| 2005/0113641 A1 | 5/2005 | Bala |
| 2005/0154262 A1 | 7/2005 | Banik et al. |
| 2005/0197536 A1 | 9/2005 | Banik et al. |
| 2005/0197658 A1 | 9/2005 | Platt |
| 2005/0213267 A1 | 9/2005 | Azrai et al. |
| 2005/0228228 A1 | 10/2005 | Boulais |
| 2005/0234296 A1 | 10/2005 | Saadat et al. |
| 2005/0277808 A1 | 12/2005 | Sonnenschein et al. |
| 2006/0004258 A1 | 1/2006 | Sun et al. |
| 2006/0004354 A1 | 1/2006 | Suslov |
| 2006/0030861 A1 | 2/2006 | Simonson et al. |
| 2006/0063973 A1 | 3/2006 | Makower et al. |
| 2006/0069303 A1 | 3/2006 | Couvillon, Jr. |
| 2006/0069313 A1 | 3/2006 | Couvillon, Jr. |
| 2006/0084839 A1 | 4/2006 | Mourlas et al. |
| 2006/0089633 A1 | 4/2006 | Bleich et al. |
| 2006/0106282 A1 | 5/2006 | Bala |
| 2006/0111613 A1 | 5/2006 | Boutillette et al. |
| 2006/0149129 A1 | 7/2006 | Watts et al. |
| 2006/0167340 A1 | 7/2006 | Pease et al. |
| 2006/0173244 A1 | 8/2006 | Boulas et al. |
| 2006/0190063 A1 | 8/2006 | Kanzius |
| 2006/0206007 A1 | 9/2006 | Bala |
| 2006/0241648 A1 | 10/2006 | Bleich et al. |
| 2006/0258951 A1 | 11/2006 | Bleich et al. |
| 2006/0270904 A1 | 11/2006 | Kupferschmid et al. |
| 2006/0276690 A1 | 12/2006 | Farris, III et al. |
| 2006/0281972 A1 | 12/2006 | Pease et al. |
| 2006/0287576 A1 | 12/2006 | Tsuji et al. |
| 2006/0293562 A1 | 12/2006 | Uchimura et al. |
| 2007/0038117 A1 | 2/2007 | Bala |
| 2007/0049794 A1 | 3/2007 | Glassenberg et al. |
| 2007/0060798 A1 | 3/2007 | Krupnik et al. |
| 2007/0073109 A1 | 3/2007 | Irion |
| 2007/0075654 A1 | 4/2007 | Kishinevsky |
| 2007/0115376 A1 | 5/2007 | Igarashi |
| 2007/0123888 A1 | 5/2007 | Bleich et al. |
| 2007/0129604 A1 | 6/2007 | Hatcher et al. |
| 2007/0129719 A1 | 6/2007 | Kendale et al. |
| 2007/0135874 A1 | 6/2007 | Bala |
| 2007/0161855 A1 | 7/2007 | Mikkaichi et al. |
| 2007/0167678 A1 | 7/2007 | Moskowitz et al. |
| 2007/0167681 A1 | 7/2007 | Gill et al. |
| 2007/0179340 A1 | 8/2007 | Jorgensen |
| 2007/0213733 A1 | 9/2007 | Bleich et al. |
| 2007/0213734 A1 | 9/2007 | Bleich et al. |
| 2007/0213735 A1 | 9/2007 | Bleich et al. |
| 2007/0225556 A1 | 9/2007 | Ortiz et al. |
| 2007/0232850 A1 | 10/2007 | Stokes et al. |
| 2007/0249904 A1 | 10/2007 | Amano et al. |
| 2007/0276183 A1 | 11/2007 | Melder |
| 2007/0287886 A1 | 12/2007 | Saadat |
| 2007/0293853 A1 | 12/2007 | Truckai et al. |
| 2008/0033465 A1 | 2/2008 | Schmitz et al. |
| 2008/0051629 A1 | 2/2008 | Sugiyama et al. |
| 2008/0051812 A1 | 2/2008 | Schmitz et al. |
| 2008/0062429 A1 | 3/2008 | Liang et al. |
| 2008/0064925 A1 | 3/2008 | Gill et al. |
| 2008/0091064 A1 | 4/2008 | Laser |

(56) References Cited

U.S. PATENT DOCUMENTS

| | | |
|---|---|---|
| 2008/0103504 A1 | 5/2008 | Schmitz et al. |
| 2008/0147018 A1 | 6/2008 | Squilla et al. |
| 2008/0161809 A1 | 7/2008 | Schmitz et al. |
| 2008/0200758 A1 | 8/2008 | Orbay et al. |
| 2008/0207992 A1 | 8/2008 | Scheller et al. |
| 2008/0207996 A1 | 8/2008 | Tsai |
| 2008/0287961 A1 | 11/2008 | Miyamoto et al. |
| 2009/0043165 A1 | 2/2009 | Kucklick et al. |
| 2009/0076329 A1 | 3/2009 | Su et al. |
| 2009/0253967 A1 | 10/2009 | Gill et al. |
| 2010/0016855 A1 | 1/2010 | Ramstein et al. |
| 2010/0022824 A1 | 1/2010 | Cybulski et al. |
| 2010/0063356 A1 | 3/2010 | Smith |
| 2010/0087798 A1 | 4/2010 | Adams et al. |
| 2010/0094231 A1* | 4/2010 | Bleich ............... A61B 17/1671 604/274 |
| 2010/0121139 A1 | 5/2010 | OuYang et al. |
| 2010/0121155 A1 | 5/2010 | OuYang et al. |
| 2010/0165335 A1 | 7/2010 | Tearney |
| 2010/0165336 A1 | 7/2010 | Ebstein |
| 2010/0217080 A1 | 8/2010 | Cheung et al. |
| 2010/0256446 A1 | 10/2010 | Raju |
| 2010/0284580 A1 | 11/2010 | OuYang et al. |
| 2010/0286477 A1 | 11/2010 | OuYang et al. |
| 2011/0009694 A1 | 1/2011 | Schultz et al. |
| 2011/0227509 A1 | 9/2011 | Saleh |
| 2011/0263933 A1 | 10/2011 | Schaaf |
| 2011/0263983 A1 | 10/2011 | Peszynski |
| 2011/0276113 A1 | 11/2011 | Cybulski |
| 2012/0071721 A1 | 3/2012 | Remijan et al. |
| 2012/0088968 A1 | 4/2012 | Gambhir et al. |
| 2012/0095458 A1 | 4/2012 | Cybulski et al. |
| 2012/0241188 A1 | 9/2012 | Power et al. |
| 2012/0265009 A1 | 10/2012 | OuYang et al. |
| 2013/0046142 A1 | 2/2013 | Remijan et al. |
| 2013/0296648 A1 | 11/2013 | OuYang et al. |
| 2013/0303846 A1 | 11/2013 | Cybulski et al. |
| 2015/0112324 A1 | 4/2015 | Cybulski |
| 2015/0157387 A1 | 6/2015 | OuYang et al. |
| 2015/0196193 A1 | 7/2015 | Kienzle et al. |
| 2015/0196197 A1 | 7/2015 | Kienzle et al. |

FOREIGN PATENT DOCUMENTS

| | | |
|---|---|---|
| CN | 101040775 A | 9/2007 |
| CN | 13961177 A | 8/2014 |
| CN | 104367296 A | 2/2015 |
| EP | 1252859 A2 | 10/2002 |
| EP | 2317931 A2 | 5/2011 |
| EP | 2451338 A2 | 5/2012 |
| GB | 2431539 A | 4/2007 |
| WO | WO 00/09001 | 2/2000 |
| WO | WO 2006/107877 | 10/2006 |
| WO | WO 2007/106740 | 9/2007 |
| WO | WO 2008/016927 | 2/2008 |
| WO | WO 2008/094436 | 8/2008 |
| WO | WO 2008/094439 | 8/2008 |
| WO | WO 2008/094444 | 8/2008 |
| WO | WO 2008/098251 | 8/2008 |
| WO | WO 2016/130844 | 8/2016 |

OTHER PUBLICATIONS

U.S. Appl. No. 15/234,999, filed Aug. 11, 2016, Washburn et al.

Keller C.A., Hinerman, R., Singh, A., Alvarez, F., "The Use of Endoscopic Argon Plasma Coagulation in Airway Complications After Solid Organ Transplantation," Chest, 2001, vol. 119, No. 6, pp. 1968-1975.

* cited by examiner

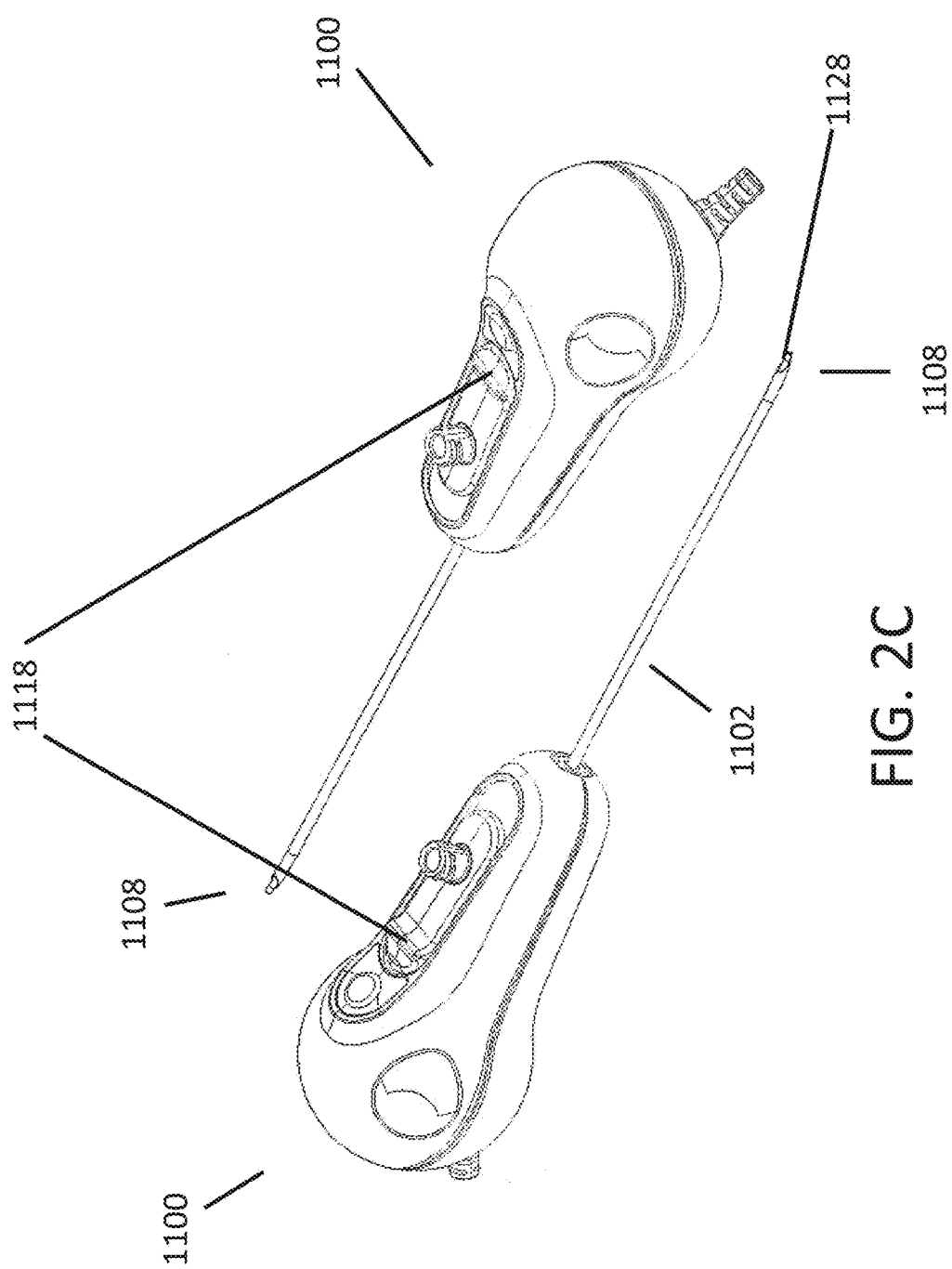

FULLY INTEGRATED, DISPOSABLE TISSUE VISUALIZATION DEVICE

CROSS-REFERENCE TO RELATED APPLICATIONS

This application claims the priority benefit under 35 U.S.C. §119(e) of U.S. Provisional Application No. 61/926,578, filed Jan. 13, 2014, the entirety of which is hereby incorporated by reference herein.

BACKGROUND OF THE INVENTION

Field of the Invention

This application describes embodiments of apparatuses, methods, and systems for the visualization of tissues.

Description of the Related Art

Traditional surgical procedures, both therapeutic and diagnostic, for pathologies located within the body can cause significant trauma to the intervening tissues. These procedures often require a long incision, extensive muscle stripping, prolonged retraction of tissues, denervation and devascularization of tissue. Such procedures can require operating room time of several hours followed by several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods.

Treatment of internal tissue sites, such as the treatment of an orthopedic joint, often requires visualization of the target internal tissues. However, proper visualization of an internal tissue site can be expensive and time-consuming to schedule, such as when magnetic resonance imaging (MRI) is required. Further, other modes of imaging can potentially damage the tissue site, leading to poor diagnosis and extended recovery time. Consequently, there is need for improved devices and methods for visualization of an internal tissue site.

SUMMARY OF THE INVENTION

Embodiments of the present invention relate to tissue visualization devices, methods, and systems. In some embodiments, tissue visualization devices comprise a visualization sensor and an elongated body having a proximal end and a distal end. The distal end of the elongated body may be dimensioned to pass through a minimally invasive body opening. In certain embodiments, the devices further comprise an integrated articulation mechanism that imparts steerability to at least one of the visualization sensor and the distal end of the elongated body. Further embodiments provide for methods of modifying the internal target tissues of a subject using tissue modification devices.

One preferred implementation of the invention is a fully integrated sterilizable disposable tissue visualization device. The device comprises a handle, and an elongate rigid tubular probe extending along a longitudinal axis between a proximal end affixed to the handle and a distal end having a sharpened tip. An image sensor is provided in the handle, and an elongate optical element extends through the probe, the optical element having a proximal end in optical communication with the sensor, and having a distal end.

A control is provided on the handle, for axially moving the tubular probe between a proximal position in which the sharpened tip is proximal to the distal end of the optical element, and a distal position in which the sharpened tip is distal to the distal end of the optical element.

An electrical cord may be integrally connected to the handle, having a free end with a connector for releasable electrical connection to an external viewing device.

The integral assembly of the handle, probe and cord may be sterilized and packaged in a single sterile container. This enables opening of the sterile container within a sterile field in a clinical environment, plugging the cord into a compatible external viewing device, and commencing a procedure on a patient without any additional assembly steps.

The distal end of the tubular probe may be provided with a lateral deflection. The deflection may be in a first direction relative to the longitudinal axis, and the cord is attached to the handle at a second direction relative to the longitudinal axis, and approximately 180° offset from the first direction. This provides visual and/or tactile feedback of the direction of the distal lateral deflection. Proximal retraction of the tubular probe deflects the distal end of the optical element laterally by at least about 1°, in some embodiments at least about 2 or 3 or 5° or more to enhance the field of view.

The optical element may comprise at least 1 and typically a plurality of optical visualization fibers and a distal lens. The optical element may additionally comprise at least one and typically a plurality of illumination optical fibers. The optical visualization fibers, optical illumination fibers and lens may be contained within a tubular body such as a hypotube.

The optical element may have an outside diameter that is spaced radially inwardly from an inside surface of the tubular probe to define an annular lumen extending the length of the tubular probe. The lumen may be in communication with an injection or an aspiration port on the handle such as for infusion of a media such as an irrigant or active agent, or for aspiration.

In one implementation of the invention, the device comprises an elongated tubular probe body comprising a 14 gauge needle (2.1 mm Outer Diameter) or outer tubular body having a sharpened distal tip. An optical hypotube is axially moveably positioned within the outer tubular body, such that it may be moved from a distal position in which it extends beyond the sharpened tip and a proximal position in which the sharpened tip is distally exposed. In certain embodiments, the optical hypotube may comprise a distal lens, image guide comprising a multi-element fiber, and additional illumination fibers all contained within a hypotube. The image guide may contain any number of suitable elements, such as 10,000 elements (e.g. fibers), while the hypotube may be of any suitable gauge, such as an 18 gauge hypotube. In some embodiments, the image guide may contain about at least 1,000 elements, at least 3,000 elements, at least 8,000 elements, at least 10,000 elements, at least 12,000 elements, at least 15,000 elements, at least 20,000 elements, at least 30,000 elements, or more than 30,000 elements. The elongated body may comprise an infusion lumen, such as an annular space between the optical hypotube and the inside diameter of the outer tubular body.

The lumen may be utilized for infusion of a therapeutic medium such as saline, liquid containing biological components such as stem cells, synthetic lubricant or other flowable media. In some embodiments, the lumen may be used to deliver saline to a tissue site or other therapeutic agents, such as growth factors, anti-bacterial molecules, or anti-inflammatory molecules.

In some embodiments, the visualization devices described herein this section or elsewhere in the specification may be used for various image guided injections beyond joint injections. For example, drugs sometimes need to be injected into the pericardium around the heart. Currently, such injections are completed blindly or with expensive visualization. As an alternative application, the visualization devices can be used when pericardial effusion occurs, a condition that occurs when too much fluid builds up around the heart. The physician can use a needle to enter the pericardial space and then drain fluid from the pericardium via a procedure known as pericardiocentesis. However, such a task could also be completed using certain embodiments of the tissue visualization devices, via penetration of the pericardium with the elongated body, followed by fluid drainage. Currently, physicians use imaging devices such as echocardiography or fluoroscopy (X ray) to guide this type of work.

The elongated body is carried by a proximal handpiece, which may be connected via cable or wireless connection to a monitor such as an iPad or other display. Output video and/or image date may be transmitted by the cable or wireless connection. The proximal hand piece includes a CCD or CMOS optical sensor, for capturing still and/or video images.

The imaging device of the present invention enables accurate positioning of the distal end of the elongated body such as within a joint capsule under direct visualization. The imaging device provides a diagnostic function, allowing a clinician or others to effectively diagnose an injury and/or condition. In embodiments, the device can also allow for reliable delivery of therapeutic media into a joint while in a physician's office under local anesthetic, thereby avoiding the need for other diagnostic procedures that may be less accurate and/or require a longer wait period.

In some embodiments, a tissue visualization device comprises:
 a handpiece comprising a visualization sensor configured to collect an image of an internal tissue site;
 at least one lens;
 an elongated body comprising a proximal end and a distal end, the elongated body comprising a lumen configured to deliver a fluid to a tissue site and an optical hypotube;
 an algorithm stored in the handpiece, the algorithm configured to correct optical aberrations in the image of the internal tissue site;
 a distal end comprising a sharpened, deflected tip.

In certain embodiments, the optical correction may be generated by comparing a captured image to a known definition pattern and generating an algorithm that corrects chromatic aberrations and image distortion specific to each individual tissue visualization device. In some embodiments, the optical correction may be unique to an individual tissue visualization device. In particular embodiments, additional information regarding the tissue visualization device may be stored, such as the X,Y position of the center of the lens, the image circle size, and unique characterisitic of the LED so as to provide a consistent initial light level. The aforementioned characteristics of the tissue visualization device and additional characteristics described elsewhere in the specification may be determined during manufacturing and stored in computer memory such as electrically erasable programmable read-only memory (EEPROM). In embodiments, the entirety of the handpiece and the elongated body may be an integrated unit. In certain embodiments, the handpiece further comprises a retraction control, configured to retract the elongated body so as to expose the distal lens of the optical hypotube. In some embodiments, the handpiece may further comprise a luer, configured to conduct fluid to the internal tissue site via the lumen.

In particular embodiments, a method of optical correction comprises:
 focusing a tissue visualization device on a known definition pattern;
 capturing an image of the known definition pattern;
 comparing the image of the known definition pattern to a reference data set corresponding to the known definition pattern;
 generating an algorithm based on the differences between the image of the known definition pattern and the known definition pattern, the algorithm configured to restore the image of the known definition pattern to the parameters of the known definition pattern;
 storing the optical correction within the tissue visualization device; and
 utilizing the optical correction to correct images collected by the tissue visualization device.

In some embodiments, the method may further comprise inserting the tissue visualization device into a tissue site and collecting an image.

In certain embodiments, a system for the visualization of a tissue site comprises:
 a fully integrated tissue visualization device including a hand piece, image sensor in the hand piece and integrated probe with fiber optics and an infusion lumen;
 a displayer configured to display images collected by the tissue visualization device; and a cable the provides for electrical communication between the displayer and the tissue visualization device.

BRIEF DESCRIPTION OF THE DRAWINGS

Other features and advantages of the present invention will be apparent from the following detailed description of the invention, taken in conjunction with the accompanying drawings of which:

FIGS. 2A-C illustrate various embodiments of a tissue visualization device.

DETAILED DESCRIPTION OF THE PREFERRED EMBODIMENTS

Figure 1:
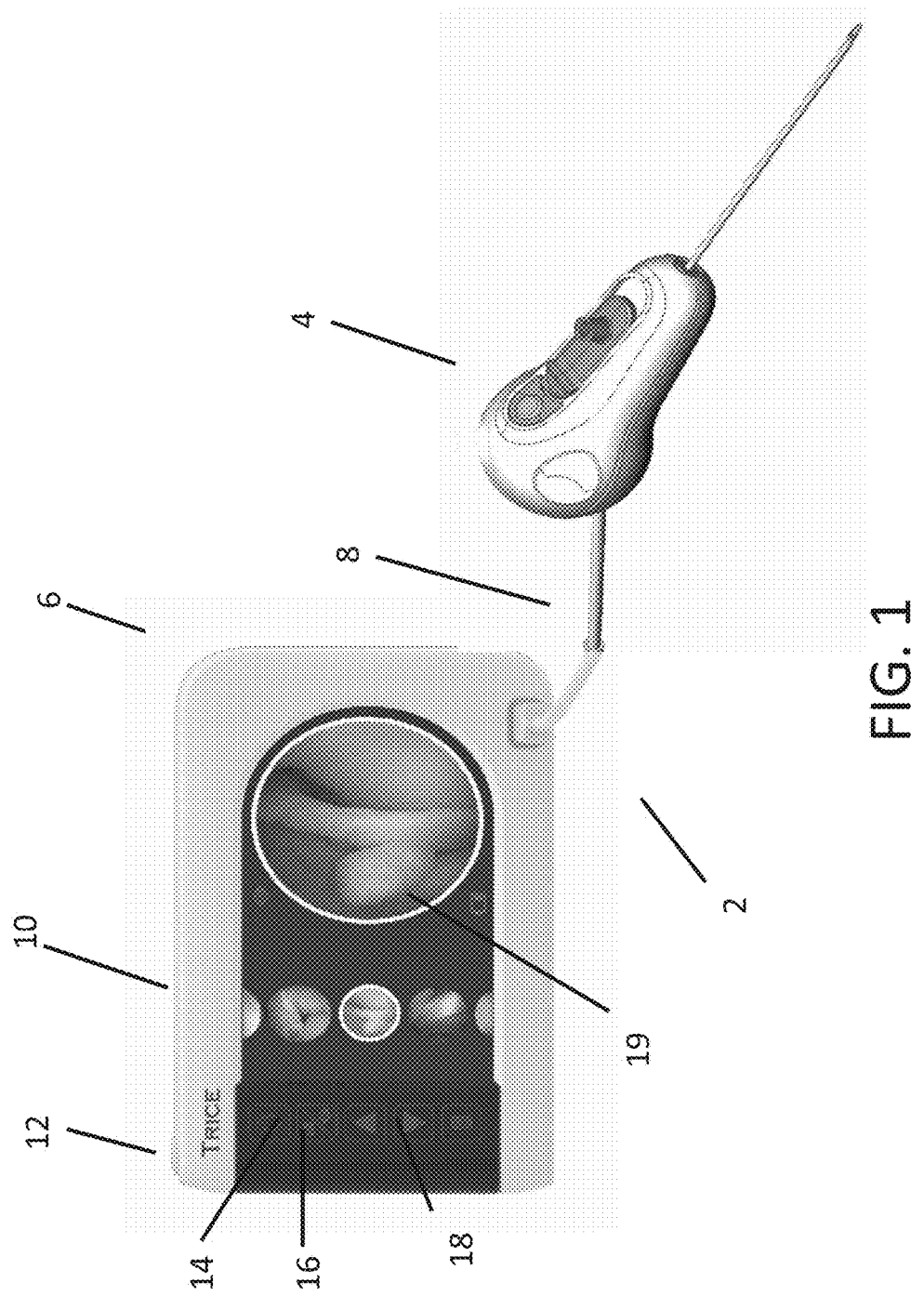
FIG. 1 illustrates an embodiment of a tissue visualization system.

Embodiments disclosed in this section or elsewhere in this application relate to minimally invasive tissue visualization and access systems and devices. Also provided are methods of using the systems in imaging applications, as well as kits for performing the methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the terms "about," "around," and "approximately." These terms are used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the invention include minimally invasive imaging and visualization systems. In some embodiments, imaging systems of the invention are minimally invasive, such that they may be introduced to an internal target site of a patient, for example, a spinal location that is near or inside of an intervertebral disc or an orthopedic joint capsule, through a minimal incision.

In some embodiments, imaging systems of the invention may include both an access device and an elongated body. The access device may be a tubular device having a proximal end and a distal end and an internal passageway extending from the proximal to distal end. Similarly, the elongated body has a proximal end and a distal end and is dimensioned to be slidably moved through the internal passageway of the access device.

In particular embodiments, access devices of the invention are elongated elements having an internal passageway that are configured to provide access to a user (e.g., a health care professional, such as a surgeon) from an extra-corporeal location to an internal target tissue site, e.g., a location near or in the spine or component thereof, e.g., near or in an intervertebral disc, inside of the disc, etc., through a minimally invasive incision. Access devices of the invention may be cannulas, components of retractor tube systems, etc. As the access devices are elongate, they have a length that is 1.5 times or longer than their width, such as 2 times or longer than their width, including 5 or even 10 times or longer than their width, e.g., 20 times longer than its width, 30 times longer than its width, or longer.

In certain embodiments, where the access devices are configured to provide access through a minimally invasive incision, the longest cross-sectional outer dimension of the access devices may (for example, the outer diameter of a tube shaped access device, including wall thickness of the access device, which may be a port or cannula in some instances) range in certain instances from 5 mm to 50 mm, such as 10 to 20 mm. With respect to the internal passageway, this passage can be dimensioned to provide passage of the imaging devices from an extra-corporeal site to the internal target tissue location. In certain embodiments, the longest cross-sectional dimension of the internal passageway, e.g., the inner diameter of a tubular shaped access device, ranges in length from 5 to 30 mm, such as 5 to 25 mm, including 5 to 20 mm, e.g., 7 to 18 mm. Where desired, the access devices are sufficiently rigid to maintain mechanical separation of tissue, e.g., muscle, and may be fabricated from any convenient material. Materials of interest from which the access devices may be fabricated include, but are not limited to: metals, such as stainless steel and other medical grade metallic materials, plastics, and the like.

The systems of the invention may further include an elongated body having a proximal and distal end, where the elongated body is dimensioned to be slidably moved through the internal passageway of the access device or directly through tissue without the use of an additional access device. As this component of the system is elongate, it has a length that is 1.5 times or longer than its width, such as 2 times or longer than its width, including 5 or even 10 times or longer than its width, e.g., 20 times longer than its width, 30 times longer than its width, or longer. When designed for use in knee joint procedures, the elongated body is dimensioned to access the capsule of the knee joint. At least the distal end of the device has a longest cross-sectional dimension that is 10 mm or less, such as 8 mm or less and including 7 mm or less, where in certain embodiments the longest cross-sectional dimension has a length ranging from 5 to 10 mm, such as 6 to 9 mm, and including 6 to 8 mm. The elongated body may be solid or include one or more lumens, such that it may be viewed as a catheter. The term "catheter" is employed in its conventional sense to refer to a hollow, flexible or semi-rigid tube configured to be inserted into a body. Catheters of the invention may include a single lumen, or two or more lumens, e.g., three or more lumens, etc, as desired. Depending on the particular embodiment, the elongated bodies may be flexible or rigid, and may be fabricated from any convenient material.

As summarized above, some embodiments of the invention include visualization sensors and illumination elements. In certain embodiments these visualization sensors are positioned within a handle at the proximal end of the device. The system may include one or more visualization sensors at the proximal end of the device and one or more illumination elements that are located among the distal and/or proximal ends of the elongated body.

Similarly, with respect to the illumination elements, embodiments of the systems include those systems where one or more illumination elements are located at the distal and/or proximal end of the elongated body. Embodiments of the systems also include those systems where one illumination element is located at the distal and/or proximal end of the elongated body and another illumination element is located at the distal and/or proximal end of the access device. Furthermore, embodiments of the systems include those systems where one or more illumination elements are located at the proximal end of the device and light is propagated via wave guides such as a fiber optic bundle towards the distal end of the device. A longest cross section dimension for the elongate body is generally 20 mm or less, 10 mm or less, 6 mm or less, such as 5 mm or less, including 4 mm or less, and even 3 mm or less.

The elongate body preferably contains an image capture waveguide, an illumination waveguide and a lumen for fluid irrigation or aspiration.

In certain embodiments, the miniature imaging sensors have a longest cross-section dimension (such as a diagonal dimension) of 20 mm or less, 10 mm or less, 5 mm or less, or 3 mm or less, where in certain instances the sensors may have a longest cross-sectional dimension ranging from 2 to 3 mm. In certain embodiments, the miniature imaging sensors have a cross-sectional area that is sufficiently small for its intended use and yet retain a sufficiently high matrix resolution. Certain imaging sensors of the may have a cross-sectional area (i.e. an x-y dimension, also known as packaged chip size) that is 2 mm×2 mm or less, such as 1.8 mm×1.8 mm or less, and yet have a matrix resolution of 400×400 or greater, such as 640×480 or greater. In some instances, the imaging sensors have a sensitivity that is 500 mV/Lux-sec or greater, such as 700 mV/Lux-Sec or greater, including 1000 mV/Lux-Sec or greater, where in some instances the sensitivity of the sensor is 2000 mV/Lux-Sec or greater, such as 3000 mV/Lux-Sec or greater. In particular embodiments, the imaging sensors of interest are those that include a photosensitive component, e.g., array of photosensitive elements, coupled to an integrated circuit, where the integrated circuit is configured to obtain and integrate the signals from the photosensitive array and output the analog data to a backend processor. The image sensors of interest may be viewed as integrated circuit image sensors, and include complementary metal-oxide-semiconductor (CMOS) sensors and charge-coupled device (CCD) sensors. In certain embodiments, the image sensors may further include a lens positioned relative to the photosensitive component so as to focus images on the photosensitive component.

Imaging sensors of interest include, but are not limited to, those obtainable from: OminVision Technologies Inc., Sony Corporation, Cypress Semiconductors. The imaging sensors may be integrated with the component of interest, e.g., the proximal handle or the elongated structure or both. In some embodiments, as the imaging sensor(s) is integrated at the proximal end of the component, it cannot be removed from the remainder of the component without significantly compromising the structure of component. As such, the integrated visualization sensor may not be readily removable from the remainder of the component, such that the visualization sensor and remainder of the component form an inter-related whole.

While any convenient imaging sensor may be employed in devices of the invention, in certain instances the imaging sensor may be a CMOS sensor. For example, the CMOS sensor may be an Aptina CMOS sensor such as the APtina MT9V124. Such a CMOS sensor may provide very small pixels, with small package sizes coupled with low-voltage differential signaling (LVDS). Such a CMOS sensor allows the cable to the display to comprise less conductors, and thus may allow for reduced cable costs as compared to other options. Of additional interest as CMOS sensors are the OmniPixel line of CMOS sensors available from OmniVision (Sunnyvale, Calif.), including the OmniPixel, OmniPixel2, OmniPixel3, OmniPixel3-HS and OmniBSI lines of CMOS sensors. These sensors may be either frontside or backside illumination sensors. Aspects of these sensors are further described in one or more the following U.S. patents, the disclosures of which are herein incorporated by reference: U.S. Pat. Nos. 7,388,242; 7,368,772; 7,355,228; 7,345,330; 7,344,910; 7,268,335; 7,209,601; 7,196,314; 7,193,198; 7,161,130; and 7,154,137.

In certain embodiments, the elongated body may further include one or more infusion lumens that run at least the substantial length of the device, e.g., for performing a variety of different functions. In certain embodiments where it is desired to flush (i.e., wash) the location of the target tissue at the distal end of the elongated body and remove excess fluid, the elongated body may include both an irrigation and aspiration lumen. During use, the irrigation lumen is operatively connected to a fluid source (e.g., physiologically acceptable fluid, such as saline) at the proximal end of the device, where the fluid source is configured to introduce fluid into the lumen under positive pressure, e.g., at a pressure ranging from 0 to 500 mm Hg, so that fluid is conveyed along the irrigation lumen and out the distal end. While the dimensions of the irrigating lumen may vary, in certain embodiments the longest cross-sectional dimension of the irrigation lumen ranges from 1 to 3 mm. During use, the aspiration lumen is operatively connected to a source of negative pressure (e.g., vacuum source) at the proximal end of the device, where the negative pressure source is configured to draw fluid from the tissue location at the distal end into the irrigation lumen under positive pressure, e.g., at a pressure ranging from 50 to 600 mm Hg, so that fluid is removed from the tissue site and conveyed along the irrigation lumen and out the proximal end, e.g., into a waste reservoir. While the dimensions of the aspiration lumen may vary, in certain embodiments the longest cross-sectional dimension of the aspiration lumen ranges from about 1 to 10 mm, about 1 to 4 mm, about 1 to 3 mm, or less than 1 mm. Alternatively, a single lumen may be provided, through which irrigation and/or aspiration may be accomplished. In embodiments, the product packaging may include a single port stopcock as a means to control fluid flow. In particular embodiments, the stopcock or suitable valve may be directly integrated into the device. In further embodiments, more than one port or stopcock may be used, such as two ports and two stopcocks, three ports and three stopcocks, and so on. In some embodiments, a three way stopcock may be provided so a clinician can 'toggle' between infusion and aspiration, or infusion of a first and second fluid, without connecting and reconnecting tubes.

In certain embodiments, the systems of the invention are used in conjunction with a controller configured to control illumination of the illumination elements and/or capture of images (e.g., as still images or video output) from the image sensors. This controller may take a variety of different formats, including hardware, software and combinations thereof. The controller may be physically located relative to the elongated body and/or access device at any convenient location such as at the proximal end of the system. In certain embodiments, the controller may be distinct from the system components, i.e., elongated body, such that a controller interface is provided that is distinct from the proximal handle, or the controller may be integral with the proximal handle.

FIG. 1 illustrates an embodiment of a system 2 for the visualization of an interior tissue site. In some embodiments, a tissue visualization system 2 comprises: a tissue visualization device 4, described in much greater detail below, a controller 6, and a cable 8 that provides electrical communication between the controller 6 and the tissue visualization device 4.

In certain embodiments, the controller 6 may comprise a housing having a memory port such as an SD card slot 10 and a camera button 12. The camera button 12 may activate the system to collect and store a still or moving image. The controller 6 may further comprise a power button 14, a mode switch button 16, and brightness controls 18. The controller 6 can further comprise a display such as a screen 19 for displaying still images and/or video.

Activating the mode switch button 10 may switch the system between different modes such as a procedure mode in which video and/or still images are collected and displayed in real-time on the video screen 19 and a consultation mode, in which a clinician may selectively display stored images and video on the video screen 19 for analysis. For example, while in procedure mode, the system could display video or images from the visualization sensor in real-time. By real-time, it is meant that the screen 19 can show video of the interior of a tissue site as it is being explored by the clinician. The video and/or images can further be stored automatically by the system for replay at a later time. For another example, while in consult mode, the screen 19 may conveniently display specific images or videos that have previously been acquired by the system, so that the clinician can easily analyze the collected images/data, and discuss the images and data with a patient. In some embodiments, the clinician may be able to annotate the images via a touch screen or other suitable means.

In certain embodiments, the screen 19 may be any type of image plane suitable for visualizing an image, such as the screen on an iPad, a camera, a computer monitor, cellular telephone or a display carried by a head worn support such as eyeglasses or other heads up display. In certain embodiments, the cable may be avoided by configuring the device and display to communicate wirelessly.

Also provided are kits for use in practicing the subject methods, where the kits may include one or more of the above devices, and/or components of the subject systems, as described above. As such, a kit may include a visualization device and a cable for connection to a controller, contained within a sterile package. The kit may further include other components, e.g., a controller, guidewires, stylets, etc., which may find use in practicing the subject methods. Various components may be packaged as desired, e.g., together or separately. Preferably, the components within the package are pre-sterilized. Further details regarding pre-sterilization of packaging may be found in U.S. Pat. No. 8,584,853, filed Feb. 16, 2013, and hereby incorporated by reference into this specification.

In addition to above mentioned components, the subject kits may further include instructions for using the components of the kit to practice the subject methods. The instructions for practicing the subject methods may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also of interest is programming that is configured for operating a visualization device according to methods of invention, where the programming is recorded on physical computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a storage medium having instructions for operating a minimally invasive in accordance with the invention.

In some embodiments, programming of the device includes instructions for operating a device of the invention, such that upon execution by the programming, the executed instructions result in execution of the imaging device to: illuminate a target tissue site, such as an orthopedic joint or portion thereof; and capture one or more image frames of the illuminated target tissue site with the imaging sensor.

Imaging sensors of interest are those that include a photosensitive component, e.g., array of photosensitive elements that convert light into electrons, coupled to an integrated circuit. The integrated circuit may be configured to obtain and integrate the signals from the photosensitive array and output image data, which image data may in turn be conveyed to an extra-corporeal display configured to receive the data and display it to a user. The image sensors of these embodiments may be viewed as integrated circuit image sensors.

The integrated circuit component of these sensors may include a variety of different types of functionalities, including but not limited to: image signal processing, memory, and data transmission circuitry to transmit data from the visualization sensor to an extra-corporeal location, etc. The miniature imaging sensors may further include a lens component made up of one or more lenses positioned relative to the photosensitive component so as to focus images on the photosensitive component. Where desired, the one or more lenses may be present in a housing. Specific types of miniature imaging sensors of interest include complementary metal-oxide-semiconductor (CMOS) sensors and charge-coupled device (CCD) sensors. The sensors may have any convenient configuration, including circular, square, rectangular, etc. Visualization sensors of interest may have a longest cross-sectional dimension that varies depending on the particular embodiment, where in some instances the longest cross sectional dimension (e.g., diameter) is 10.0 mm or less, such as 6.0 mm or less, including 3.0 mm or less.

Imaging sensors of interest may be either frontside or backside illumination sensors, and have sufficiently small dimensions while maintaining sufficient functionality to be integrated at the proximal end of the elongated bodies within the hand piece of the devices of the invention. Aspects of these sensors are further described in one or more the following U.S. patents, the disclosures of which are herein incorporated by reference: U.S. Pat. Nos. 7,388,242; 7,368,772; 7,355,228; 7,345,330; 7,344,910; 7,268,335; 7,209,601; 7,196,314; 7,193,198; 7,161,130; and 7,154,137.

The distal end of the elongate body may be configured for front viewing and/or side-viewing, as desired. In yet other embodiments, the elongate body may be configured to provide image data from both the front and the side, e.g., where the primary viewing axis from the distal end of the waveguide extends at an angle that is greater than about 2° or 5° or 10° or 15° or more relative to the longitudinal axis of the elongated body, described in greater detail below.

Depending on the particular device embodiment, the elongated body may or may not include one or more lumens that extend at least partially along its length. When present, the lumens may vary in diameter and may be employed for a variety of different purposes, such as irrigation, aspiration, electrical isolation (for example of conductive members, such as wires), as a mechanical guide, etc., as reviewed in greater detail below. When present, such lumens may have a longest cross section that varies, ranging in some instances from 0.5 to 5.0 mm, such as 1.0 to 4.5 mm, including 1.0 to 4.0 mm. The lumens may have any convenient cross-sectional shape, including but not limited to circular, square, rectangular, triangular, semi-circular, trapezoidal, irregular, etc., as desired. These lumens may be provided for a variety of different functions, including as irrigation and/or aspiration lumens, as described in greater detail below.

In certain embodiments, the devices may include one or more illumination elements configured to illuminate a target tissue location so that the location can be visualized with a visualization sensor, e.g., as described above. A variety of different types of light sources may be employed as illumination elements, so long as their dimensions are such that they can be positioned at or carry light to the distal end of the elongated body. The light sources may be integrated with a given component (e.g., elongated body) such that they are configured relative to the component such that the light source element cannot be removed from the remainder of the component without significantly compromising the structure of the component. As such, the integrated illumination element of these embodiments is not readily removable from the remainder of the component, such that the illumination element and remainder of the component form an interrelated whole. The light sources may be light emitting diodes configured to emit light of the desired wavelength range, or optical conveyance elements, e.g., optical fibers, configured to convey light of the desired wavelength range from a location other than the distal end of the elongated body, e.g., a location at the proximal end of the elongated body within the hand piece, to the distal end of the elongated body.

As with the image sensors, the light sources may include a conductive element, e.g., wire, or an optical fiber or bundle, which runs the length of the elongated body to provide for power and control of the light sources from a location outside the body, e.g., an extracorporeal control device.

Where desired, the light sources may include a diffusion element to provide for uniform illumination of the target tissue site. Any convenient diffusion element may be employed, including but not limited to a translucent cover or layer (fabricated from any convenient translucent material) through which light from the light source passes and is thus diffused. In those embodiments of the invention where the system includes two or more illumination elements, the illumination elements may emit light of the same wavelength or they may be spectrally distinct light sources, where by "spectrally distinct" is meant that the light sources emit light at wavelengths that do not substantially overlap, such as white light and infra-red light. In certain embodiments, an illumination configuration as described in U.S. application Ser. Nos. 12/269,770 and 12/269,772 (the disclosures of which are herein incorporated by reference) is present in the device.

In some embodiments, devices of the invention may include a linear mechanical actuator for linearly translating a distal end element of the device, such as a tubular needle which surrounds a visualization element relative to the visualization element. By "linearly translating" is meant moving the along a substantially straight path. As used herein, the term "linear" also encompasses movement in a non-straight (i.e., curved) path.

In some embodiments, an integrated articulation mechanism that imparts steerability to the distal end of the elongated body and/or distal end of the visualization element is also present in the device. By "steerability" is meant the ability to maneuver or orient the visualization element, tissue modifier and/or distal end of the elongated body as desired during a procedure, e.g., by using controls positioned at the proximal end of the device. In these embodiments, the devices include a steerability mechanism (or one or more elements located at the distal end of the elongated body) which renders the desired distal end component maneuverable as desired through proximal end control. As such, the term "steerability", as used herein, refers to a mechanism that provides a user steering functionality, such as the ability to change direction in a desired manner, such as by deflecting the primary viewing axis left, right, up or down relative to the initial axial direction.

The steering functionality can be provided by a variety of different mechanisms. Examples of suitable mechanisms include, but are not limited to one or more axially moveable pull or push wires, tubes, plates, meshes or combinations thereof, made from appropriate materials, such as shape memory materials, music wire, etc. In some instances, the distal end of the elongated body is provided with a distinct, additional capability that allows it to be independently rotated about its longitudinal axis when a significant portion of the operating handle is maintained in a fixed position, as discussed in greater detail below.

The extent of distal primary viewing axis articulations of the invention may vary, such as from at least about 5°, 10°, 25°, or 35° or more from the primary viewing axis. The visualization element may be configured for rotating about its axis so that the full range of angles is accessible on either side of the axis of the probe, essentially multiplying the effective viewing angle e.g., as described in greater detail below. Articulation mechanisms of interest are further described in published PCT Application Publication Nos. WO 2009029639; WO 2008/094444; WO 2008/094439 and WO 2008/094436; the disclosures of which are herein incorporated by reference. Specific articulation configurations of interest are further described in connection with the figures, below.

In certain embodiments, devices of the invention may further include an irrigator and aspirator configured to flush an internal target tissue site and/or a component of the device, such as a lens of the visualization sensor. As such, the elongated body may further include one or more lumens that run at least the substantial length of the device, e.g., for performing a variety of different functions, as summarized above. In certain embodiments where it is desired to flush (i.e., wash) the target tissue site at the distal end of the elongated body (e.g. to remove ablated tissue from the location, etc.), the elongated body may include both irrigation lumens and aspiration lumens. Thus, the tissue modification device can comprise an irrigation lumen extending axially through the elongated body. During use, the irrigation lumen may be operatively connected to a fluid source (e.g., a physiologically acceptable fluid, such as saline) at the proximal end of the device, where the fluid source is configured to introduce fluid into the lumen under positive pressure, e.g., at a pressure ranging from 0 psi to 60 psi, so that fluid is conveyed along the irrigation lumen and out the distal end. While the dimensions of the irrigation lumen may vary, in certain embodiments the longest cross-sectional dimension of the irrigation lumen ranges from 0.5 mm to 5 mm, such as 0.5 mm to 3 mm, including 0.5 mm to 1.5 mm.

During use, the aspiration lumen may be operatively connected to a source of negative pressure (e.g., a vacuum source) at the proximal end of the device. While the dimensions of the aspiration lumen may vary, in certain embodiments the longest cross-sectional dimension of the aspiration lumen ranges from 1 mm to 7 mm, such as 1 mm to 6 mm, including 1 mm to 5 mm. In some embodiments, the aspirator comprises a port having a cross-sectional area that is 33% or more, such as 50% or more, including 66% or more, of the cross-sectional area of the distal end of the elongated body.

In some instances, the negative pressure source is configured to draw fluid and/or tissue from the target tissue site at the distal end into the aspiration lumen under negative pressure, e.g., at a negative pressure ranging from 300 to 600 mmHg, such as 550 mmHg, so that fluid and/or tissue is removed from the tissue site and conveyed along the aspiration lumen and out the proximal end, e.g., into a waste reservoir. In certain embodiments, the irrigation lumen and aspiration lumen may be separate lumens, while in other embodiments, the irrigation lumen and the aspiration functions can be accomplished in a single lumen.

In certain embodiments, the devices may include a control structure, such as a handle, operably connected to the proximal end of the elongated body. By "operably connected" is meant that one structure is in communication (for example, mechanical, electrical, optical connection, or the like) with another structure. When present, the control structure (e.g., handle) is located at the proximal end of the device. The handle may have any convenient configuration, such as a hand-held wand with one or more control buttons, as a hand-held gun with a trigger, etc., where examples of suitable handle configurations are further provided below.

In some embodiments, the distal end of the elongated body is rotatable about its longitudinal axis when a significant portion of the operating handle is maintained in a fixed position. As such, at least the distal end of the elongated body can turn by some degree while the handle attached to the proximal end of the elongated body stays in a fixed position. The degree of rotation in a given device may vary, and may range from 0 to 360°, such as 0 to 270°, including 0 to 180°.

As described herein this section and elsewhere in the specification, in certain embodiments, the device may be disposable or reusable. As such, devices of the invention may be entirely reusable (e.g., be multi-use devices) or be entirely disposable (e.g., where all components of the device are single-use). In some instances, the device can be entirely reposable (e.g., where all components can be reused a limited number of times). Each of the components of the device may individually be single-use, of limited reusability, or indefinitely reusable, resulting in an overall device or system comprised of components having differing usability parameters.

As described herein this section and elsewhere in the specification, in certain embodiments, devices of the invention may be fabricated using any convenient materials or combination thereof, including but not limited to: metallic materials such as tungsten, stainless steel alloys, platinum or its alloys, titanium or its alloys, molybdenum or its alloys, and nickel or its alloys, etc.; polymeric materials, such as polytetrafluoroethylene, polyimide, PEEK, and the like; ceramics, such as alumina (e.g., STEATITE™ alumina, MAECOR™ alumina), etc.

With respect to imaging the interior of a joint capsule methods include positioning a distal end of the visualization element of the invention in viewing relationship to the target tissue. By viewing relationship is meant that the distal end is positioned within 40 mm, such as within 10 mm, including within 5 mm of the target tissue site of interest. Positioning the distal end in viewing device in relation to the desired target tissue may be accomplished using any convenient approach, including direct linear advance from a percutaneous access point to the target tissue. Following positioning of the distal end of the imaging device in viewing relationship to the target tissue, the target tissue is imaged through use of the illumination and visualization sensors to obtain image data. Image data obtained according to the methods of the invention is output to a user in the form of an image, e.g., using a monitor or other convenient medium as a display means. In certain embodiments, the image is a still image, while in other embodiments the image may be a video.

In embodiments, the internal target tissue site may vary widely. Internal target tissue sites of interest include, but are not limited to, orthopedic joints, cardiac locations, vascular locations, central nervous system locations, etc. In certain cases, the internal target tissue site comprises spinal tissue. Orthopedic joints may comprise any type of joint of interest within the human body, such as the knee or the shoulder. In some embodiments, the internal tissue site may comprise sites of interest during general surgery, such as abdominal organs and/or surrounding tissues.

Further applications of the tissue visualization devices described herein this section or elsewhere in the specification include use in general surgery (laparoscopic or other minimally invasive surgery) as a secondary visualization device. Sometimes the laparoscopic camera needs to be removed and procedure is blind. But the outer diameters of the devices described herein this application are so small that they can be used to eliminate the blackout once a laparoscopic camera is removed. Although in many of the embodiments described herein, the elongated body is rigid, however the fiber is flexible and can be mounted in an elongated flexible tubular body with any of a variety of steering mechanisms such as one or two or three or more pull wires to deflect the distal end. In some embodiments, the device may comprise a biased curved distal end (e.g., Nitinol) that can be selectively curved or straightened by retracting an outer straight sleeve or internal straightening wire, etc.

Beyond general surgery and the other applications described herein this section and elsewhere in the specification, embodiments of the visualization devices described herein can be utilized in ear nose and throat applications. For example, the devices described herein may be used in any diagnostic evaluation where visualization may be valuable. As another example, the devices described herein may also be used to guide or evaluate the treatment of chronic sinusitis, for instance, the dilatation of a sinus such as the maxillary sinus.

In some embodiments, the subject devices and methods find use in a variety of different applications where it is desirable to image and/or modify an internal target tissue of a subject while minimizing damage to the surrounding tissue. The subject devices and methods find use in many applications, such as but not limited to surgical procedures, where a variety of different types of tissues may be visualized and potentially treated, including but not limited to; soft tissue, cartilage, bone, ligament, etc. Additional methods in which the imaging devices find use include those described in United States Published Application No. 20080255563.

In one implementation of the invention, the imaging device is utilized to accurately position the distal end of a needle within the joint capsule in, for example, a knee. This enables injection of therapeutic media into the capsule on a reliable basis. For this application, the outside diameter of the tubular body has a diameter of less than about 3 mm, preferably less than about 2.5 mm and, in one implementation, approximately 2.1 mm (14 gauge).

Figure 2A:
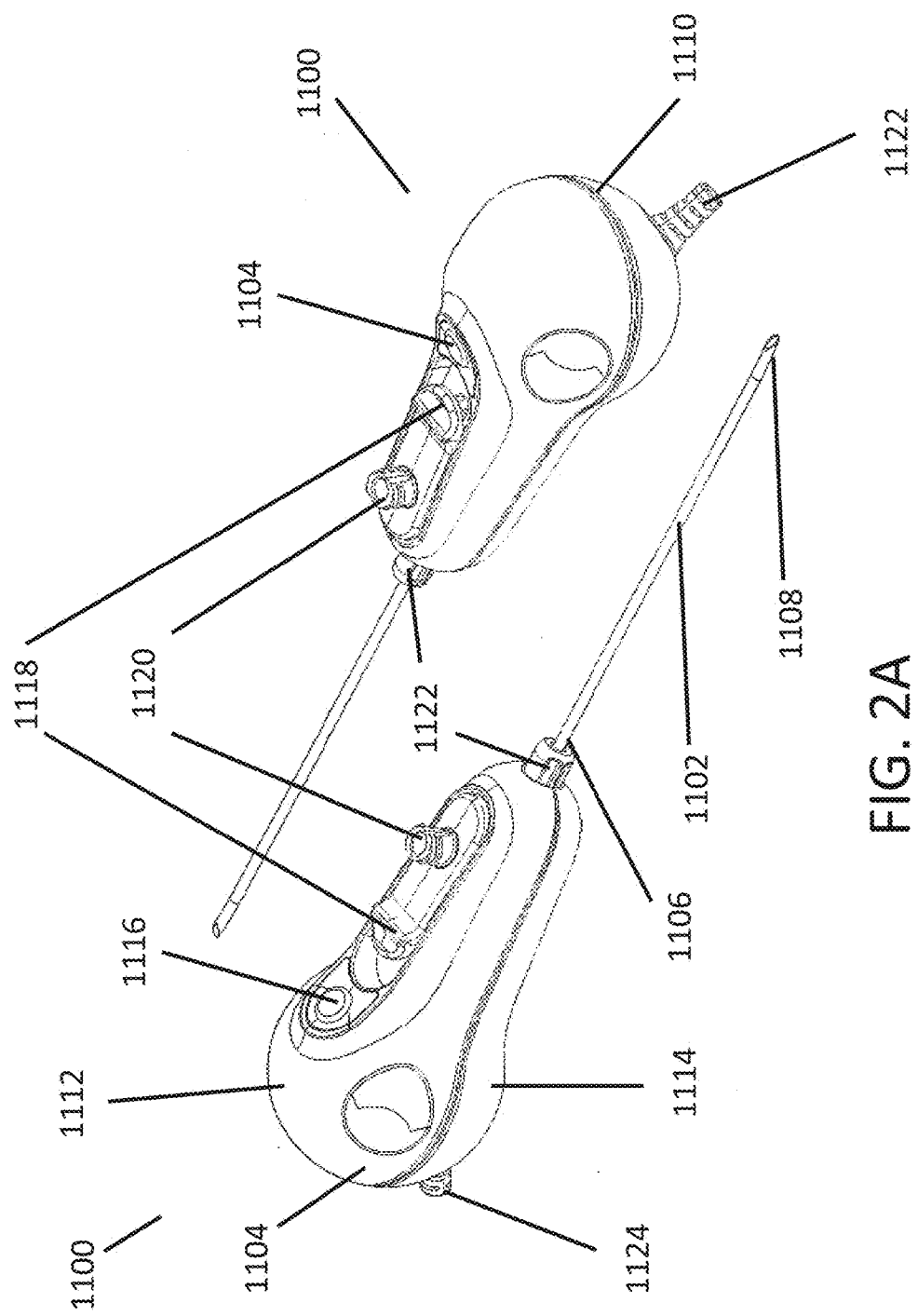

FIG. 2A illustrates an embodiment of a tissue visualization device 1100, comprising an elongated body 1102 and a handpiece 1104. The elongated body may have a length that is at least around 1.5 times longer than its width, at least around 2 times longer than its width, at least around 4 times longer than its width, at least around 10 times or longer than its width, at least around 20 times longer than its width, at least around 30 times longer than its width, at least around 50 times longer than its width, or longer than 50 times the width. The length of the elongated body may vary, and in some instances may be at least around 2 cm long, at least around 4 cm long, at least 6 cm long, at least 8 cm long, at least 10 cm long, at least 15 cm long, at least 20 cm long, at least 25 cm, at least 50 cm, or longer than 50 cm. The elongated body may have the same outer cross-sectional dimensions (e.g., diameter) along its entire length. Alternatively, the cross-sectional diameter may vary along the length of the elongated body. In certain embodiments, the outer diameter of the elongated body is approximately 0.1 to 10 mm, approximately 0.5 mm to 6 mm, approximately 1 mm to 4 mm, approximately 1.5 mm to 3 mm, approximately 2 mm to 2.5 m, or approximately 2.1 mm. In certain embodiments, the elongated body is a 14 gauge needle, having an OD of about 2.1 mm and a ID of about 1.6 mm.

In certain embodiments, the elongated body may have a proximal end 1106 and a distal end 1108. The term "proximal end", as used herein, refers to the end of the elongated body that is nearer the user (such as a physician operating the device in a tissue modification procedure), and the term "distal end", as used herein, refers to the end of the elongated body that is nearer the internal target tissue of the subject during use. The elongated body is, in some instances, a structure of sufficient rigidity to allow the distal end to be pushed through tissue when sufficient force is applied to the proximal end of the elongated body. As such, in these embodiments the elongated body is not pliant or flexible, at least not to any significant extent. In certain embodiments, the distal end 1108 can further comprise a sharpened tip as depicted in FIG. 2A, allowing the distal end to pierce through tissue such as a joint capsule.

As depicted in FIG. 2A, in embodiments, the handpiece may have a rounded "clamshell" shape comprising a seam 1110 connecting a clamshell top 1112 and a clamshell bottom 1114. In some embodiments, the clamshell top 1112 and bottom 1114 and can be manufactured in two pieces and then attached together at the seam 1110. The rounded clamshell shape provides a comfortable and ergonomic handle for a user to hold while using the device. In certain embodiments and as will be described in greater detail later, the handpiece may comprise an image capture control such as a button 1116 configured to capture a desired image. In further embodiments, the image capture control may comprise a switch, dial, or other suitable mechanism. The handpiece 104 may further comprise a retraction control 1118 that retracts or extends a portion of the elongated body 1102 such as a sharpened needle. The retraction control will be described in greater detail in relation to FIGS. 2B-C and later Figures.

In certain embodiments, the control 1116 may selectively activate the acquisition of an image and/or video. The control 1116 may thus be configured to selectively start video recording, stop video recording, and capture a still image either during video recording or while video recording is off. In some embodiments, the control or another control may turn on/off an ultraviolet light (UV) source that would be used with UV sensitive material such as a gel. For example, a UV-sensitive liquid could be delivered to a target tissue, such as the knee, followed by application of UV liquid to solidify the liquid into a solid or semi-solid material. UV light may be generated via a standard LED, such as those described elsewhere in the specification. The UV light could be directed towards the target tissue via illumination fibers such as those described elsewhere in the specification, while still retaining some illumination fibers to illuminate the target tissue for the purposes of imaging.

In embodiments, the handpiece may comprise a luer connection 1120, configured to connect to any fluid source as described herein this section or elsewhere in this specification, such as sterile saline. The luer connection 1120 may be in fluid communication with a lumen extending throughout the length of the elongated body, allowing for the delivery of fluid or agents to the tissue site.

The junction between the handpiece 1104 and the elongated body 1102 may include a hub 1122 that connects the handpiece 1104 to the elongated body 1102. In some embodiments, the hub may be detachable, allowing the elongated body to be detached from the handpiece. In other embodiments, the elongated body is permanently attached to the handpiece via the hub to provide an integrated assembly.

The handpiece may further comprise a strain relief node 1124, configured to attach to an electrical cable (not shown in FIG. 2A). The strain relief node 1124 can serve to reduce strain on electrical wiring that may be in electrical communication with the handpiece.

In some embodiments, the tissue visualization device 1100 is configured as an integrated assembly for one time use. In certain embodiments, the tissue visualization device 1100 is pre-sterilized, thus the combination of integration and pre-sterilization allows the tissue visualization device to be ready for use upon removal from the packaging. Following use it is disposed. Thus the handpiece 1104, elongated body 1102, and other components, such as the cable, may be all one integrated unit. By one integrated unit, it is meant that the various portions described above may be attached together as one single piece not intended for disassembly by the user. In some embodiments, the various portions of the integrated unit are inseparable without destruction of one or more components. In some embodiments, the display, as described herein this section or elsewhere in the specification, may also be incorporated and sterilized as part of a single integrated tissue visualization device.

Figure 2B:
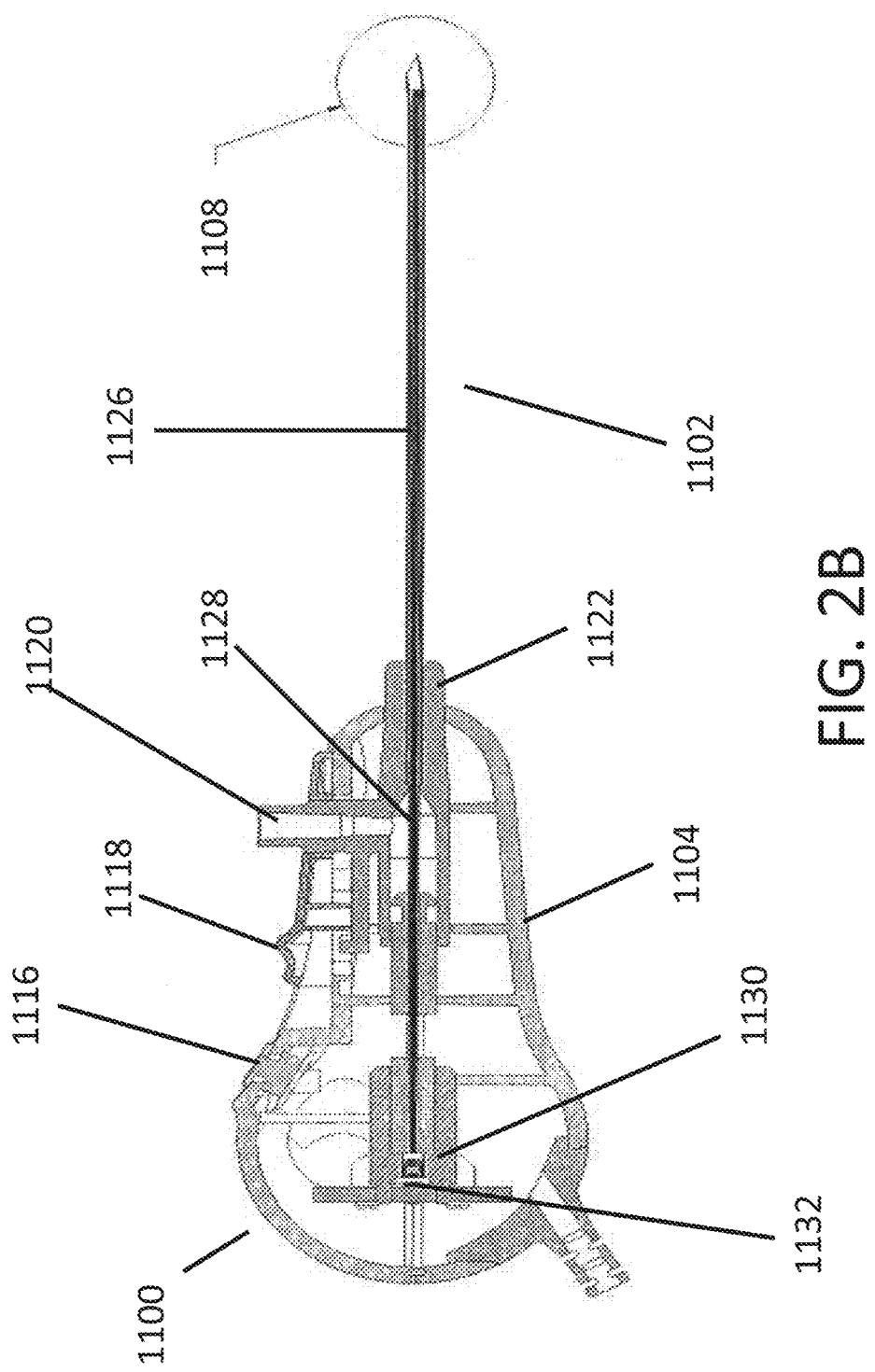

FIG. 2B illustrates a cross-sectional side view of an embodiment of the tissue visualization device depicted in FIG. 2A. As in FIG. 2A, the tissue visualization device comprises a number of components such as an image capture trigger 1116, retraction control 1118, luer 1120, elongated body 1102, handpiece 1104, and hub 1122.

In some embodiments, the distal end 1108 may comprise a deflected configuration, in which the distal end of the elongated body inclines away from the longitudinal axis of the elongated body 1102. This deflected tip is preferably sharpened, allowing the tip to penetrate a tissue site of interest. The deflected tip embodiment of the distal end 1108 will be described below in greater detail in relation to FIGS. 3A-B.

Figure 3A:
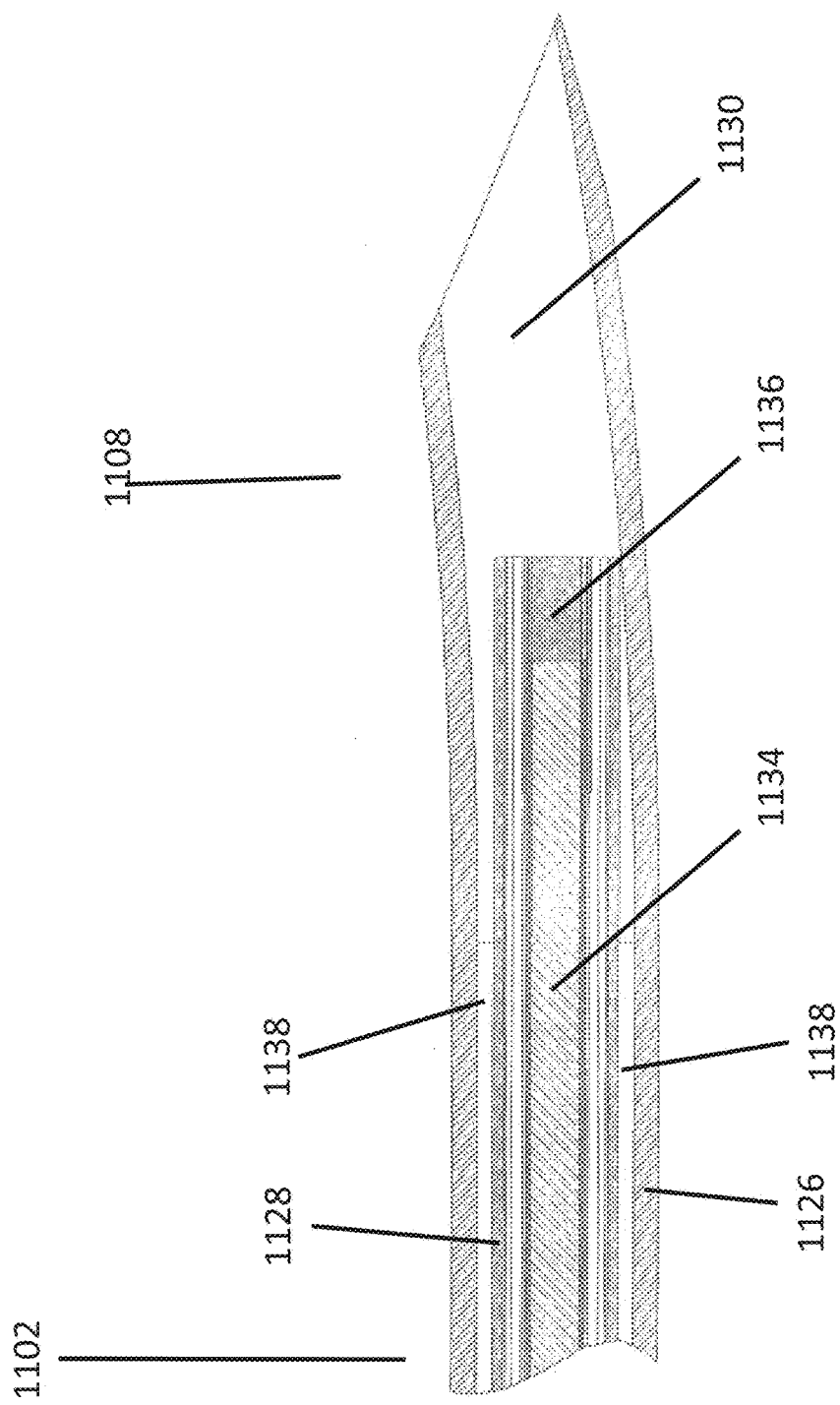
FIGS. 3A-B illustrate close-up cross-sectional side views of embodiments of the distal end of the tissue visualization device illustrated in FIG. 2A.
Figure 3B:
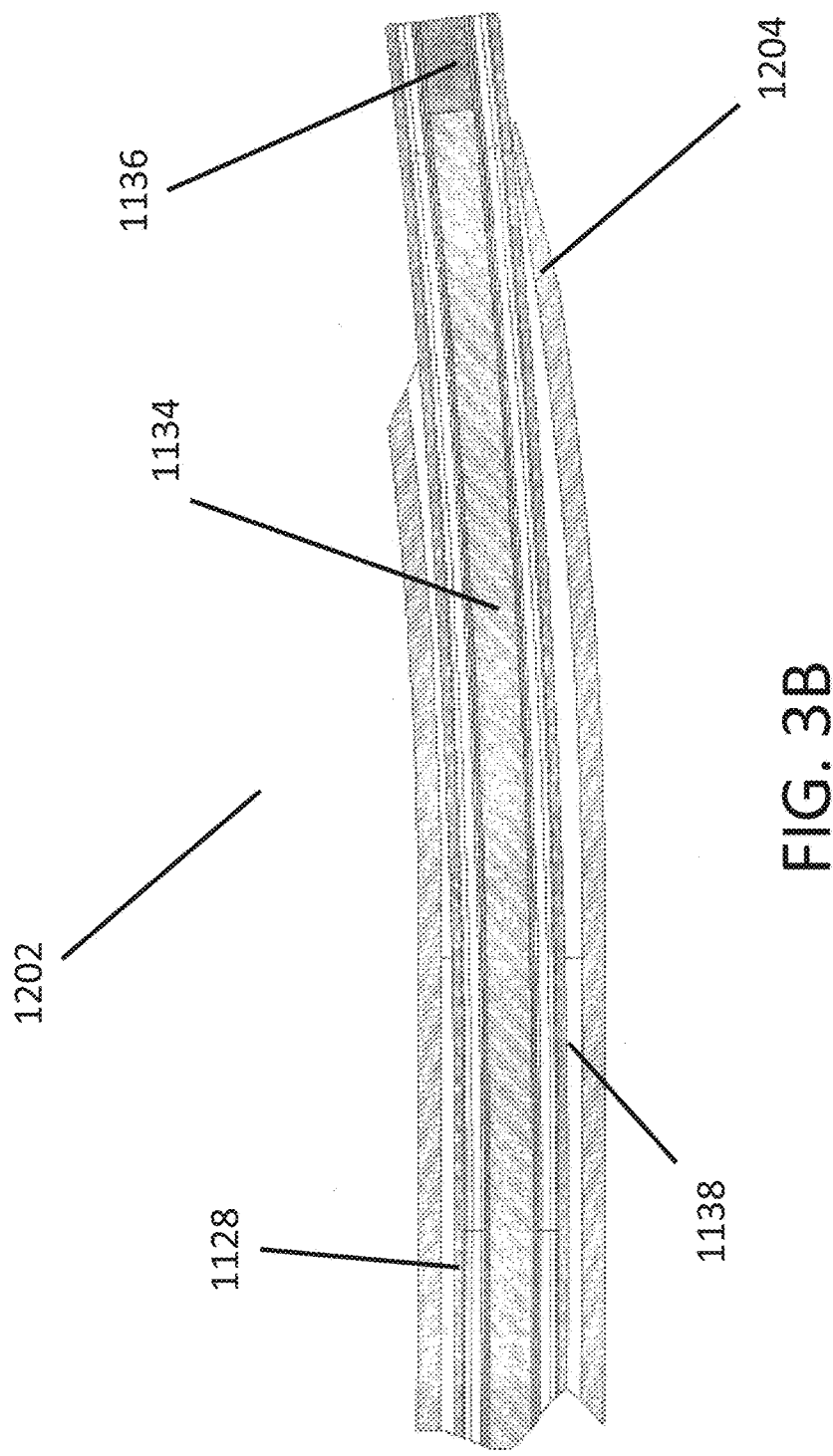

As can now be seen in FIG. 3A, the elongated body 1102 comprises an outer tubular body 1126 which may be a hypodermic needle such as a 14 gauge needle with a sharpened tip. The visualization element is in the form of an inner optical hypotube 1128 extending concentrically through the outer tubular body 1126. The optical hypotube can act to transmit an image of a tissue site to a visualization sensor 1132 (FIG. 2B) such as those described herein this section and elsewhere in the specification. The handpiece 1104 further comprises a proximal lens housing 1130, described in more detail below in FIG. 7.

Referring to FIGS. 2C and 3A, as described above, in some embodiments the handpiece may comprise a retraction control 1118. The retraction control can serve to retract the outer tubular body 1126 of FIG. 3A, relative to the optical hypotube, thus allowing the optical hypotube to extend beyond the front opening of the outer tubular body at the distal end 1108. See FIG. 3B. In some embodiments, the sharpened distal end is used to pierce the tissue to direct the elongated body into the target area. Once the elongate body has reached the target area, such as within the joint capsule the retraction control 118 can then be used to retract the sharpened tip proximally of the distal end of the visualization element. By retracting the sharpened tip, it allows the user to direct the now blunt distal end of the elongated body within a tissue site without risk of piercing the tissue again. Retraction of the sharpened tip can be particularly useful for certain tissue sites. For example, once a distal end has pierced the joint capsule of an orthopedic joint, there is risk of piercing through the opposite end of the joint capsule. By retracting the sharpened end, images of the joint capsule can be captured and medication injected without fear of further damaging the joint capsule.

In certain embodiments, the edges and sides of the elongated body and tip are blunted so as not to damage the surrounding tissue while inserting the elongated body. Blunting of the sharp edges from both the axial end and the side are critical as the integrated nature of the device results in the sharp edges being exposed to the interior anatomy. Typically a blunt cannula has a removable trocar which provides access through the tissue. The trocar is then replaced with a separate camera hypotube.

In some embodiments, blunting is accomplished with the deflected geometry of the needle biasing the optical hypotube against the inner diameter of the needle. Furthermore, the needle has a reverse grind that further "protects" the sharp edge as it is directly against the OD of the optical hypotube. Another embodiment would be to have a straight needle and some kind of geometry (dimples) on either the needle or optical hypotube that would bias the OD of the optical hypotube against the ID of the Needle.)

FIG. 3A depicts an embodiment of the distal end 1108 of the elongated body 1102 similar to the embodiments described in FIGS. 2A-C. The elongated body 1102 may be in the extended position, such as illustrated in FIG. 3A, allowing the sharpened tip of the distal end 1108 to pierce the tissue of interest as described herein this section or elsewhere in the specification. As described above, while in the retracted position 1202 (FIG. 3B), the elongated body is less likely to further damage the tissue site. Further, the sharpened distal end of the elongated body 1108 may have a lateral deflection relative to the longitudinal axis of the elongated body 1102, resulting in a deflected tip 1130. In further embodiments, the tip may be straight. The deflection may be in an upward direction when the handpiece is oriented as in FIG. 2B with the controls on the top. Deflection may be at least about 1 degree, 3 degrees, 7 degrees, 12 degrees, 15 degrees or more from the axis of the elongated body.

The deflected tip 1130 allows a mechanical means of altering the direction of view of the optical hypotube (such as about 5-6 degrees). In some embodiments, the direction of view may be at least about 3 degrees, at least about 6 degrees, at least about 12 degrees, at least about 15 degrees, at least about 20 degrees, at least about 30 degrees, at least about 45 degrees, or greater than 45 degrees off the axis of the optical hypotube. Wide angle field of view can be accomplished with a lens, or by rotating the fiber optic if the distal end is deflected off axis. The deflected tip may also provides better directional performance during insertion and limits the "coring" associated with traditional needle geometry (minimizing the chance that a skin core would be dragged into the patient and potentially cause an infection).

In some embodiments, the elongated body 1102 comprises a lumen 1138 that may deliver fluid including medications such as anti-inflammatory agents, antibiotics, anesthetics or others known in the art within the capsule or to other tissue site. In certain embodiments, as depicted in FIG. 3A, the lumen 1138 may encompass the annular space between the optical hypotube 1128, and the outer tubular body 1126.

In some embodiments, the distal end of the visualization element may comprise a distal lens 1136 configured to facilitate the imaging of an internal tissue site. The distal lens, or any other lens, may develop defects and imperfections during manufacturing, leading to a distortion in the image. These distortions may be unique to individual lenses and thus in the case of the embodiments disclosed herein this application, may be unique to an individual tissue visualization device. Thus, to enhance image quality, the device 1100 as depicted in FIG. 2A, may include an automatic optical correction in the form of a unique algorithm. In some embodiments, the algorithm may be stored in a chip or other suitable means within the handpiece 1004.

In certain embodiments, the automatic optical correction may serve to improve the image quality generated by the tissue visualization device. The Abbe number, also known as the V-number or constringence of a transparent material, is a measure of the material's dispersion (variation of refractive index with wavelength) in relation to the refractive index, with high values of V indicating low dispersion (low chromatic aberration). Low chromatic aberration is desired to optimize image quality, but achieving that normally increases manufacturing cost. In some embodiments, chromatic aberrations in the tissue visualization device may be corrected via the aforementioned software algorithm at the time of clinical use, which allows economies during manufacturing. For example, the optical correction may allow for visualization performance from the device with less expensive lenses that rivals the performance of visualization devices that use far more expensive lenses with minimal imperfections.

In embodiments, to generate the algorithm at the point of manufacture, the distal optic is focused on a known definition pattern. A computer can then compare the captured image to the known pattern and create an algorithm that restores the captured image to the true definition pattern. As described above, that algorithm may then be stored in a chip in the handpiece 1104.

When the handpiece 1104 is connected to a displayer 6 at the clinical site, as described previously in relation to FIG. 1, the algorithm serves as the basis for the displayer 6 to correct the captured image such that aberrations in the optical system are removed. Each individual tissue visualization device will have unique aberrations, so each handpiece will carry a unique algorithm designed to correct that system.

Returning to FIG. 3B, FIG. 3B further depicts a closer view of an embodiment of the sharpened distal end 1204 of the elongated body in the retracted position. As described above, in relation to FIG. 2C, the retraction control serves to retract the sharpened deflected tip 1204 to prevent further damage to the surrounding tissue while viewing an interior tissue site.

Figure 4:
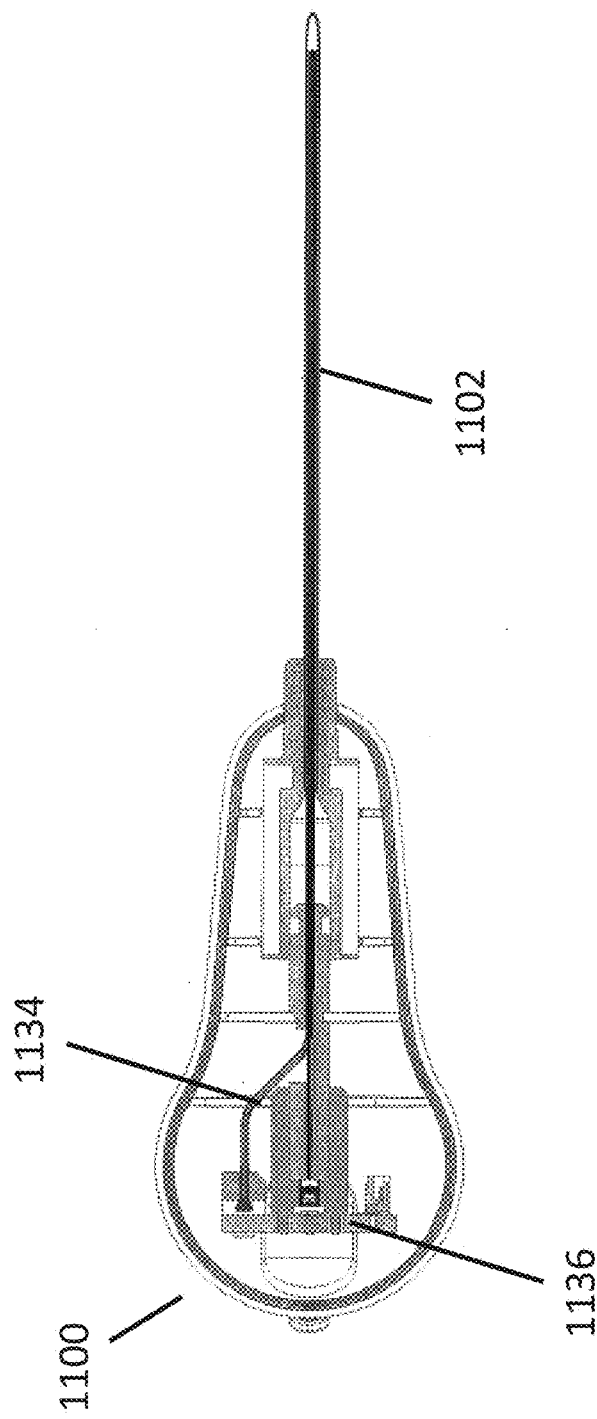
FIG. 4 illustrates a cross-sectional top view of an embodiment of a tissue visualization and modification device

FIG. 4 depicts a cross-sectional top view of an embodiment of the tissue visualization device 1100. The handpiece 1104 comprises an illumination element 1134 and a visualization sensor support 1136, described in greater detail below. Similar to illumination elements or apparatuses described elsewhere in this specification, the illumination element 1134 may extend down the length of the elongated body and convey light down the elongated body to an interior tissue site to allow for visualization of the target tissue. In some embodiments, the illumination element 1134 comprises a bundle of illumination fibers.

Figure 5:
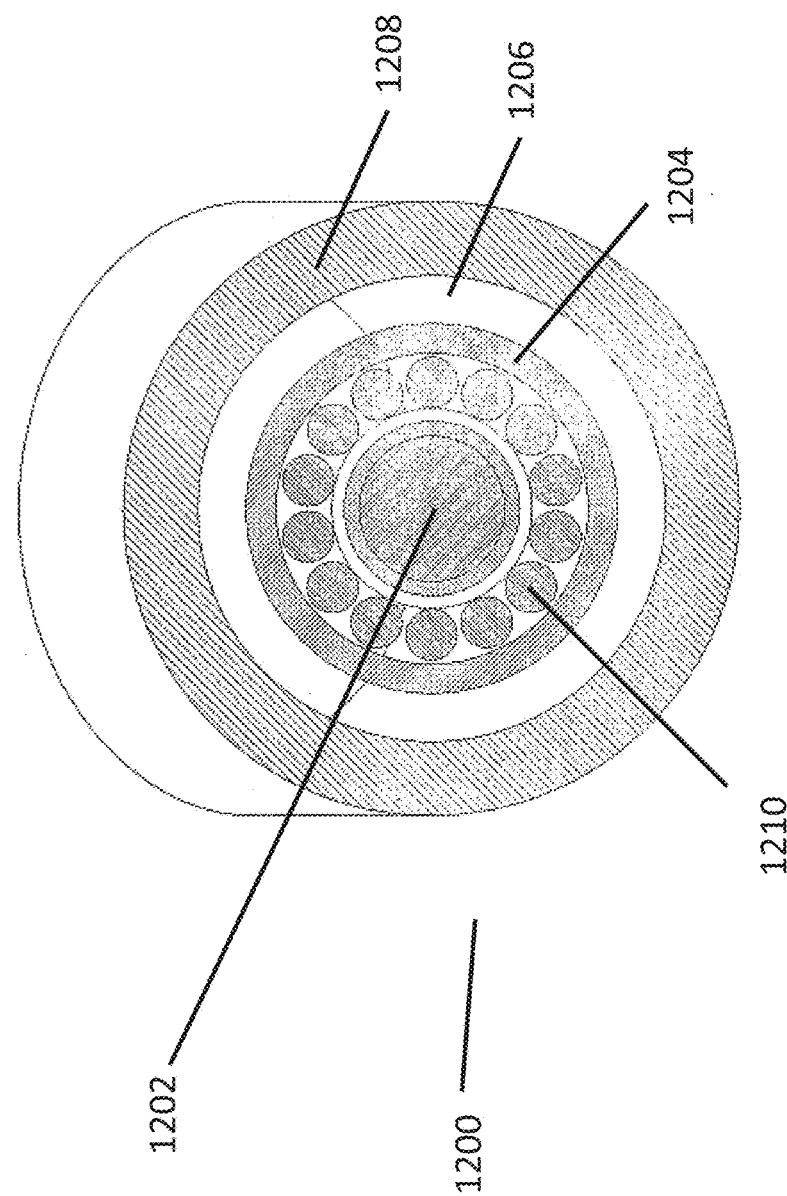
FIG. 5 illustrates a cross-sectional view of a tubular portion of a tissue visualization and modification device.

FIG. 5 illustrates cross sectional views of an embodiment of a tissue visualization device down the length of an elongated body 1200, similar to the elongated bodies depicted in FIGS. 2A-4. In certain embodiments, the optical hypotube 1204 may comprise an image guide 1202, at least one illumination fiber or fiber bundle 1210, an infusion lumen 1206, and outer tubular body 1208. As will be understood by one skilled in the art, the use of the term "illumination fiber" here encompasses an illumination fiber or fiber bundle. As described elsewhere in the specification, the illumination fibers or fiber bundles may be configured to transmit a wavelength of light suitable for illuminating a target tissue for visualization; however, the illumination fibers may also be configured to transmit UV light to a tissue site for the purpose of solidifying a UV-sensitive material. For example, if there are 14 total illumination fibers or fiber bundles, then 7 may be configured to deliver light suitable for visualization while another 7 may be suitable for delivering UV light. However, any suitable combination may be used. For example, most of the illumination fibers may be UV, half of the illumination fibers, or less than half. In particular embodiments, the number of illumination fibers may be increased or decreased from the number depicted in FIG. 5. For example, there may be one fiber, at least two fibers, at least 5 fibers, at least 10 fibers, at least 14 fibers, at least 20 fibers, at least 25 fibers, at least 50 fibers, or more than 50 fibers. In certain embodiments, the illumination fibers may be configured to output multiple wavelengths of light suitable for imaging an internal tissue site.

The wavelength of light delivered via illumination fibers 1210 [which can be at least 4, 8, 12 or more fibers or bundles of fibers, and which may be arranged in an annular configuration surrounding the image guide 1202 as shown in FIG. 5 but described in detail below] may be selected for various wavelength specific applications. For example, wavelengths in the UV range can be utilized to permit visual differentiation of tissue types such as to distinguish nervous tissue from surrounding tissue and/or minimally vascularized nervous tissue. Blood vessels may appear to have a first color (such as red) while nerve tissue may appear to have a second color (such as blue). The wavelength may also be optimized to distinguish nervous tissue from muscle.

In another application, light such as UV light or visible light may be propagated via fiber 1210 to promote or initiate curing of an infused solution (e.g., via polymerization or cross-linking), where the solution or gel is administered via infusion lumen 1206, to form a solid or semi-solid mass in vivo. The mass may be a tissue bulking device, coating layer or other structural element.

Another wavelength specific application involves directing a preselected wavelength to a target impregnated with a drug or drug precursor. Upon delivery of the preselected wavelength to the target, drug is caused to be released, or the precursor is converted into a drug which is then released. The target may be an implanted mass or device, or an infused carrier medium such as any or a combination of a liquid, gel, or beads.

The UV light may include Ultraviolet A, long wave, or black light, abbreviated "UVA" and having a wavelength of 400 nm-315 nm; Near UV light, abbreviated "NUV" and having a wavelength of 400 nm-300 nm; Ultraviolet B or medium wave, abbreviated "UVB" and having a wavelength of 315 nm-280 nm; Middle UV light, abbreviated "MUV" and having a wavelength of 300 nm-200 nm; Ultraviolet C, short wave, or germicidal, abbreviated "UVC" and having a wavelength of 280 nm-100 nm; Far UV light, abbreviated "FUV" and having a wavelength of 200 nm-122 nm; Vacuum UV light, abbreviated "VUV" and having a wavelength of 200 nm-400 nm; Low UV light, abbreviated "LUV" and having a wavelength of 100 nm-88 nm; Super UV light, abbreviated "SUV" and having a wavelength of 150 nm-10 nm; and Extreme UV light, abbreviated "EUV" and having a wavelength of 121 nm-10 nm. In some embodiments, the catheters may include an element that emits visible light. Visible light may include violet light having a wavelength of 380-450 nm; blue light having a wavelength of 450-475 nm; cyan light having a wavelength of 476-495 nm; green light having a wavelength of 495-570 nm; yellow light having a wavelength of 570-590 nm; orange light having a wavelength of 590-620 nm; and red light having a wavelength of 620-750 nm. In some embodiments, the catheter includes an element that emits light having a wavelength between about 300 nm and 500 nm. In particular, the catheter may include an element that emits light having a wavelength associated with blue light (e.g., light having a wavelength between about 450-475 nm). Wavelength selection information and characterization and other details related to infrared endoscopy are found in U.S. Pat. No. 6,178,346; US Patent Application Publication No. 2005/0014995, and US Patent Application Publication No. 2005/0020914, each of which is hereby incorporated by reference in its entirety.

In certain embodiments, the outer diameter of the optical hypotube may range from approximately 0.1 mm to 3 mm, approximately 0.5 mm to 2.5 mm, or approximately 1 mm to 2 mm. In certain embodiments, the outer diameter of the optical hypotube is approximately 1.27 mm. In some embodiments, the inner diameter of the outer tubular body ranges from approximately 0.1 mm to 10 mm, approximately 0.2 mm to 8 mm, approximately 0.5 mm to 6 mm, approximately 1 mm to 5 mm, approximately 1.2 mm to 4 mm, or approximately 1.4 mm to 3 mm. In certain embodiments, the inner diameter of the outer tubular body 1208 is approximately 1.6 mm.

In some embodiments, the image guide 1202 allows for the viewing of an image of the tissue site by the visualization sensor in the handpiece. In particular embodiments, the image guide may be a fiber optic or other suitable medium to allow for imaging of the tissue site by a visualization sensor as described herein this section or elsewhere in the specification. The fiber optic bundle may have at least about 6K, or at least about 10K or at least about 15K or at least about 30K fibers or more, depending upon the desired performance. In some embodiments, the image fiber may be a 6.6 k fiber bundle or a 10 k fiber bundle.

Figure 6A:
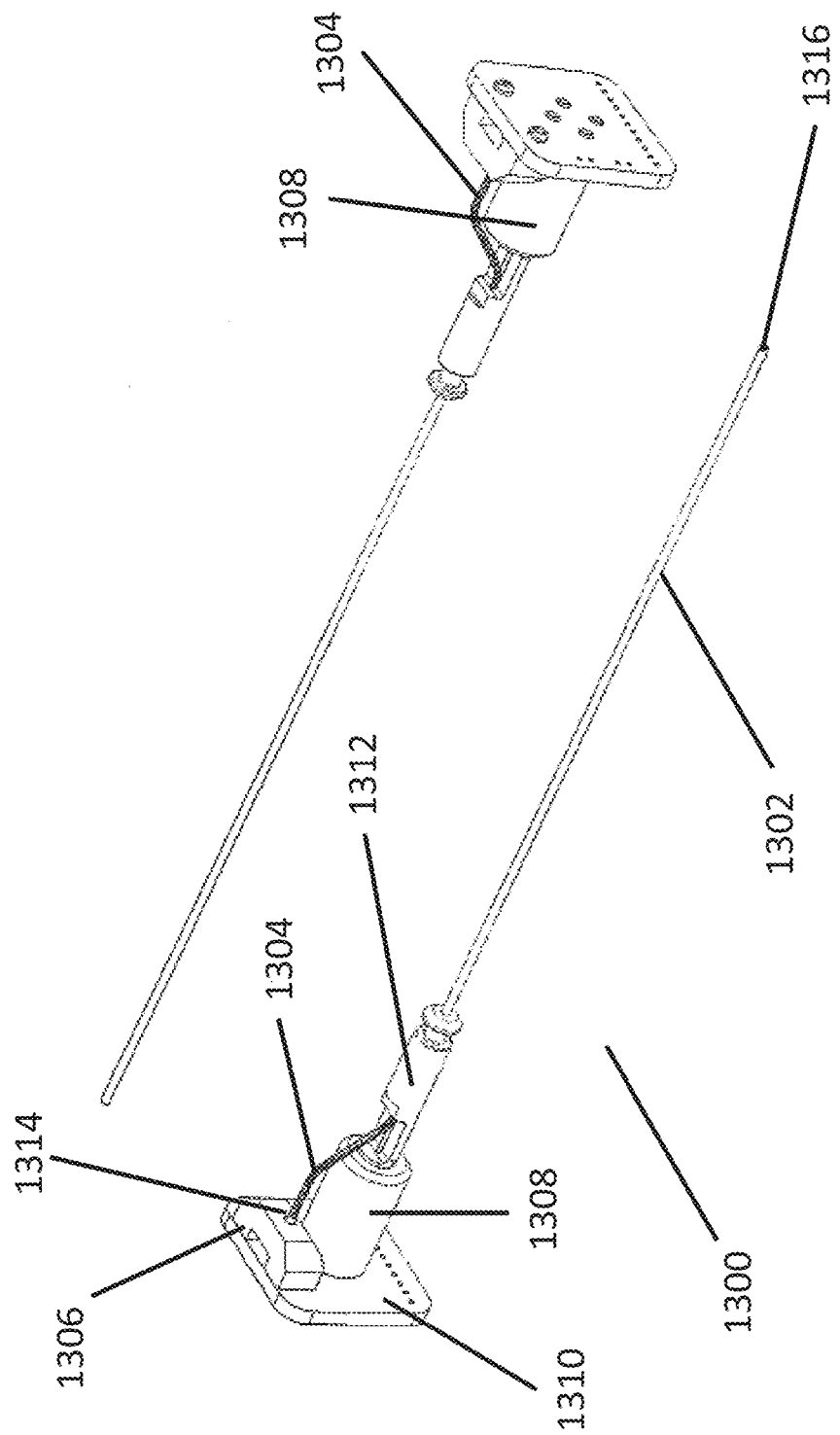
FIGS. 6A-C illustrate embodiments of a tissue visualization device with the outer housing removed.
Figure 6B:
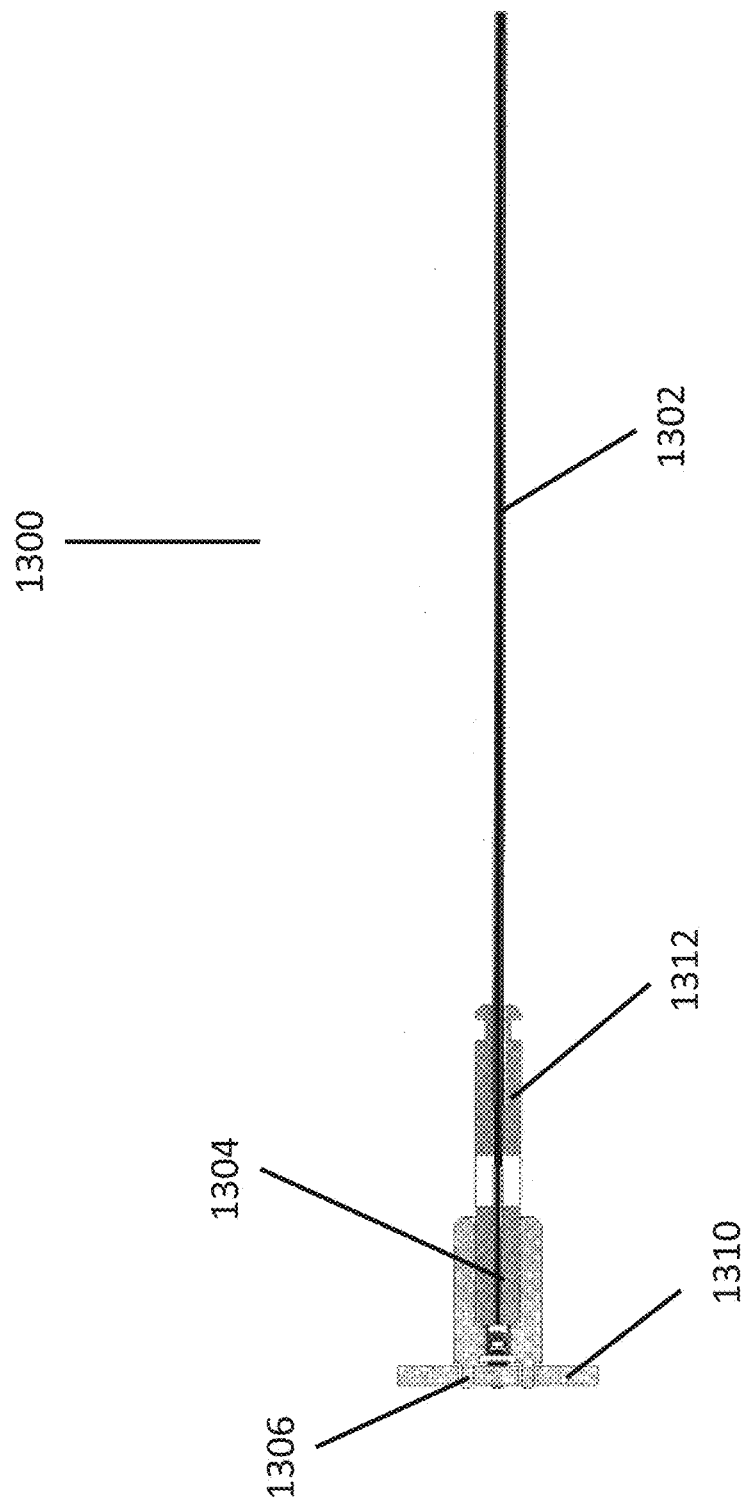
Figure 6C:
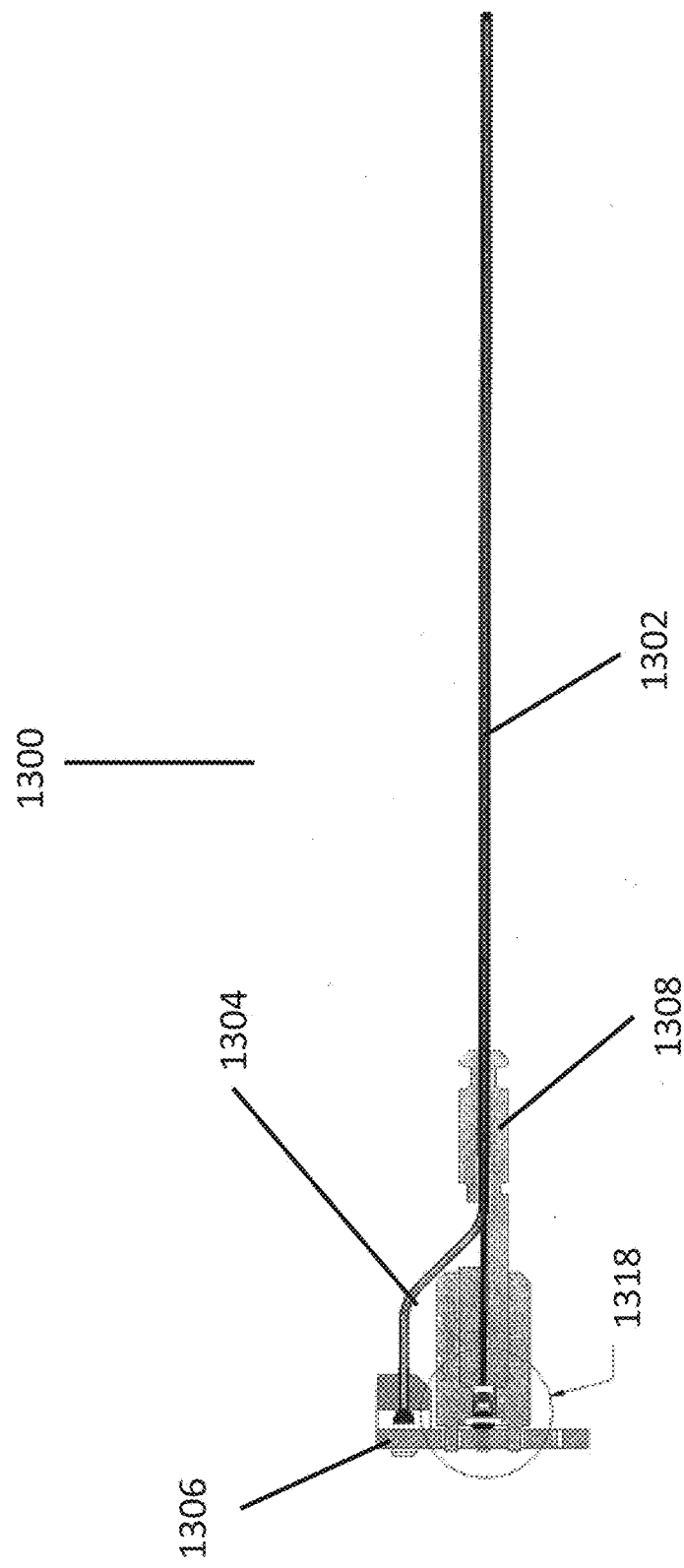

FIGS. 6A-C illustrate embodiments of the elongated body and inner components of a tissue visualization device 1300, similar to the embodiments depicted elsewhere herein. In this particular figure, the outer shell of the handpiece is removed to better view the interior of the device. In certain embodiments, the tissue visualization device comprises an elongated body 1302, an illumination element 1304, light source housing 1306, a proximal lens housing 1310, a ferrule 1314, a nosepiece 1312, and a distal lens 1316.

FIG. 6B illustrates a top view of the tissue visualization device 1300 of FIG. 6A, while FIG. 6C illustrates a side view. The components in these figure are similar to the components illustrated in 6A, however in 6B, the visualization complex is identified as 1318. The visualization complex and surrounding components can be viewed in more detail in FIG. 7.

Figure 7:
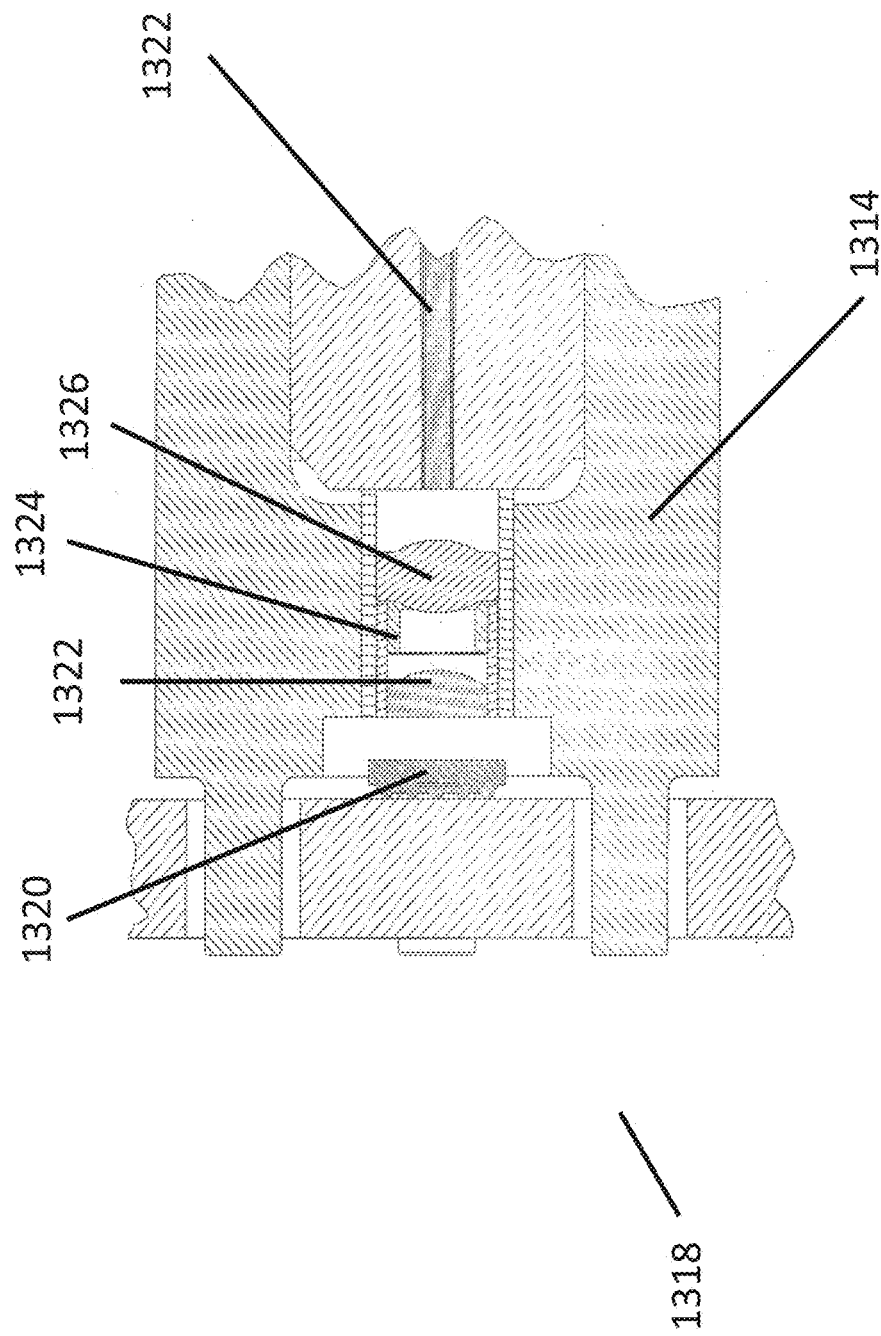
FIG. 7 illustrates a cross-sectional side view of an embodiment of the lens housing depicted in FIG. 6A-C.

FIG. 7 illustrates a cross-sectional side view of an embodiment of the visualization complex of FIG. 6C. In some embodiments, the visualization complex 1318 may comprise a visualization sensor 1320 such as those visualization sensors described herein this section or elsewhere in the specification. In certain embodiments, the visualization sensor may be a CMOS sensor as described herein this section or elsewhere in the specification.

In certain embodiments, the visualization complex can comprise a first lens 1322, an optical aperture 1324, and a second lens 1326. In some embodiments, the aperture may have a diameter of at least about 0.1 mm, at least about 0.2 mm, at least about 0.3 mm, at least about 0.5 mm, or more than 0.5 mm. Preferably, the aperture may be approximately 0.222 mm. To support the lenses, the visualization complex may comprise a proximal lens housing as described previously, wherein the proximal lens housing may serve to secure the lenses 1320 and 1326 in the proper location and orientation. The visualization complex may further comprise an image guide, similar to the image guide described previously in relation to FIG. 5.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described in this section or elsewhere in this specification may be embodied in a variety of other forms. Furthermore, various omissions, substitutions and changes in the form of the methods and systems described in this section or elsewhere in this specification may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth in this section or elsewhere in this specification. Accordingly, the scope of the present disclosure is not intended to be limited by the specific disclosures of preferred embodiments in this section or elsewhere in this specification, and may be defined by claims as presented in this section or elsewhere in this specification or as presented in the future.

What is claimed is:

1. A sterilized, integrated, one time use disposable visualization needle, comprising:
   an elongate tubular needle, extending along a longitudinal axis between a proximal end affixed to a handpiece and a distal end having a sharpened tip;
   an elongate optical element extending through the needle;
   wherein an outer diameter of the distal end of the elongate optical element is configured to have a bias against an inner diameter of a point of the sharpened tip of the needle, the bias configured to press the distal end of the elongate optical element against the distal end of the elongate tubular needle to provide blunting of the tubular needle.

2. The visualization needle of claim 1, further comprising an image sensor, the image sensor configured to be in optical communication with the elongate optical element.

3. The visualization needle of claim 2, wherein illumination is provided by a plurality of LEDs positioned in the optical element adjacent to the image sensor.

4. The visualization needle of claim 1, wherein the sharpened tip comprises a reverse grind, the reverse grind providing blunting at an outer diameter of the needle and sharpening at an inner diameter of the needle.

5. The visualization needle of claim 1, wherein the handpiece comprises a control for axially moving the elongate tubular needle between a proximal position in which the sharpened tip is proximal to a distal end of the optical element, and a distal position in which the sharpened tip is distal to the distal end of the optical element.

6. The visualization needle of claim 1, wherein the blunting is configured to prevent damage to a tissue site.

7. The visualization needle of claim 1, wherein axial proximal movement of the elongate tubular needle deflects a distal end of the optical element laterally by at least about 3 degrees.

8. The visualization needle of claim 1, wherein the optical element has an outside diameter that is smaller than an inside diameter of the tubular needle to define a lumen extending the length of the elongate tubular needle, the lumen configured to provide aspiration or irrigation to the distal end of the elongate tubular needle.

9. The visualization needle of claim 8, wherein the lumen is in communication with an injection or aspiration port located in the handpiece.

10. The visualization needle of claim 1, wherein the handpiece is configured to wirelessly communicate with an external viewing device.

11. The visualization needle of claim 1, wherein the handpiece further comprises a memory chip comprising an algorithm configured to correct an image artifact.

12. The visualization needle of claim 11, wherein the algorithm is uniquely generated for an individual visualization needle.

13. The visualization needle of claim 1, wherein the handpiece further comprises a memory chip configured to store data on the characteristics of the visualization needle.

14. The visualization needle of claim 13, wherein the characteristics are selected from the group consisting of LED illumination performance data, correction algorithms for correction of a lens, and correction information for chromatic aberrations of an image sensor.

15. The visualization needle of claim 1, wherein the distal end of the optical element is configured to provide illumination.

16. The visualization needle of claim 15, wherein illumination is provided by a plurality of LEDs located at the distal end of the optical element.

17. The visualization needle of claim 16, wherein the LEDs are configured to provide light in a wavelength outside the visible spectrum.

18. The visualization needle of claim 17, wherein the LEDs are configured to provide light in the UV spectrum.

19. The visualization needle of claim 15, wherein illumination is provided by a plurality of LEDs located in the handpiece.

20. The visualization needle of claim 15, wherein illumination is provided by an infrared light source.

21. The visualization needle of claim 1, wherein the distal end of the optical element comprises a diffusion element, the diffusion element configured to provide uniform illumination.

22. The visualization needle of claim 1, further comprising an integrated articulation mechanism, the integrated articulation mechanism configured to provide movement to the distal end of the optical element.

23. The visualization needle of claim 22, wherein the distal end of the elongate tubular needle is configured to be curved or straightened by the integrated articulation mechanism.

24. The visualization needle of claim 23, wherein the integrated articulation mechanism comprises pull wires.

25. The visualization needle of claim 23, wherein the distal end of the elongate tubular needle is configured to rotate about the longitudinal axis.

26. The visualization needle of claim 1, wherein the distal end of the elongate tubular needle comprises an articulating tip, the articulating tip configured to move toward and away from the longitudinal axis, the articulating tip further configured to rotate about the longitudinal axis.

27. The visualization needle of claim 1, wherein the distal end of the elongate tubular needle is deflected away from the longitudinal axis, the distal end of the elongate tubular needle configured to rotate about the longitudinal axis.

28. The visualization needle of claim 1, wherein the distal end of the elongate optical element is configured to rotate about the longitudinal axis.

29. The visualization needle of claim 1, wherein the distal end of the elongate tubular needle is configured to rotate about the longitudinal axis.

* * * * *

UNITED STATES PATENT AND TRADEMARK OFFICE
CERTIFICATE OF CORRECTION

PATENT NO. : 9,610,007 B2
APPLICATION NO. : 15/187583
DATED : April 4, 2017
INVENTOR(S) : Richard A. Kienzle It is certified that error appears in the above-identified patent and that said Letters Patent is hereby corrected as shown below:

In the Specification

Column 3 Line 64, Change "characterisitic" to --characteristic--.

Column 4 Line 55, After "device" insert --.--.

Column 4 Line 61, Change "FIG." to --FIGS.--.

Column 7 Line 64, Change "OminVision" to --OmniVision--.

Column 8 Line 13, Change "APtina" to --Aptina--.

Column 18 Line 16, Change "Needle.)" to --Needle.--.

Signed and Sealed this
Twentieth Day of February, 2018

Andrei Iancu
*Director of the United States Patent and Trademark Office*